(12) United States Patent
Liu et al.

(10) Patent No.: US 11,046,684 B2
(45) Date of Patent: Jun. 29, 2021

(54) COMPOUND FOR SELECTIVELY INHIBITING KINASE AND USE THEREOF

(71) Applicant: SHANGHAI ZHEYE BIOTECHNOLOGY LIMITED-LIABILITY COMPANY, Shanghai (CN)

(72) Inventors: Jianyu Liu, Shanghai (CN); Haidong Zhang, Shanghai (CN)

(73) Assignee: SHANGHAI ZHEYE BIOTECHNOLOGY LIMITED LIABILITY COMPANY, Shanghai (CN)

( * ) Notice: Subject to any disclaimer, the term of this patent is extended or adjusted under 35 U.S.C. 154(b) by 0 days.

(21) Appl. No.: 16/474,991

(22) PCT Filed: Dec. 29, 2017

(86) PCT No.: PCT/CN2017/120224
§ 371 (c)(1),
(2) Date: Jun. 28, 2019

(87) PCT Pub. No.: WO2018/121774
PCT Pub. Date: Jul. 5, 2018

(65) Prior Publication Data
US 2019/0359610 A1    Nov. 28, 2019

(30) Foreign Application Priority Data
Jan. 2, 2017 (CN) .......................... 201710000367.7

(51) Int. Cl.
*C07D 471/04* (2006.01)
*A61P 35/00* (2006.01)

(52) U.S. Cl.
CPC ............ *C07D 471/04* (2013.01); *A61P 35/00* (2018.01)

(58) Field of Classification Search
CPC .............................. C07D 471/04; A61P 35/00
(Continued)

(56) References Cited

FOREIGN PATENT DOCUMENTS

| CN | 104011051 A | 8/2014 |
|---|---|---|
| CN | 105683188 A | 6/2016 |

OTHER PUBLICATIONS

International Application No. PCT/CN2017/120224, International Search Report and Written Opinion, dated Mar. 26, 2018.
(Continued)

*Primary Examiner* — Taylor V Oh
(74) *Attorney, Agent, or Firm* — Marshall, Gerstein & Borun LLP

(57) ABSTRACT

Provided are a compound of formula (I), a stereoisomer, a tautomer or a pharmaceutically acceptable salt thereof, use thereof as a selective inhibitor for FGFR4 kinase and use thereof in manufacturing a medicament or pharmaceutical composition for treating diseases due to FGFR4 or FGF19. The compound disclosed by the invention has selective and significant inhibitory activities against FGFR4, and has wide application prospect in the field of tumor treatment.

(Continued)

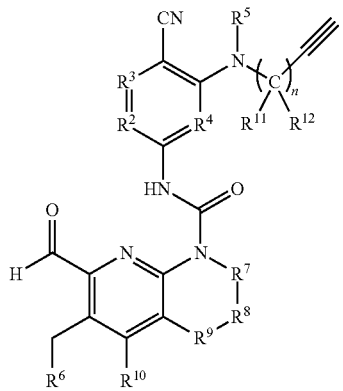

(I)

13 Claims, 3 Drawing Sheets

(58) Field of Classification Search
USPC .......................................................... 546/122
See application file for complete search history.

(56) References Cited

OTHER PUBLICATIONS

International Application No. PCT/CN2017/120224, International Preliminary Report on Patentability, dated Mar. 26, 2018.
Mo, C., et al., "2-Aminopyrimidine Derivatives as New Selective Fibroblast Growth Factor Receptor 4 (FGFR4) Inhibitors," *ACS Medicinal Chemistry Letters*, 2017. 8(5): p. 543-548.
Tiong, K.H., et al., "Fibroblast growth factor receptor 4 (FGFR4) and fibroblast growth factor 19 (FGF19) autocrine enhance breast cancer cells survival," *Oncotarget*, 2016. 7(36): p. 57633-57650.
Zhang, X., et al., "Increased Expression of FGF19 Contributes to Tumor Progression and Cell Motility of Human Thyroid Cancer," *Otolaryngology—Head and Neck Surgery*, 2016. 154(1): p. 52-58.
Wang, S., et al., "FGF19 Contributes to Tumor Progression in Gastric Cancer by Promoting Migration and Invasion," *Oncology Research Featuring Preclinical and Clinical Cancer Therapeutics*, 2016. 23(4): p. 197-203.
Feng, S., et al., "Endocrine Fibroblast Growth Factor FGF19 Promotes Prostate Cancer Progression," *Cancer research*, 2013. 73(8): p. 2551-2562.
Huang, H.-p., et al., "The prognostic significance of fibroblast growth factor receptor 4 in non-small-cell lung cancer," *OncoTargets and therapy*, 2015. 8: p. 1157-1164.
Zaid, T.M., et al., "Identification of FGFR4 as a Potential Therapeutic Target for Advanced-Stage, High-Grade Serous Ovarian Cancer," *Clinical Cancer Research*, 2013. 19(4): p. 809-820.
Xu, Y.-F., et al., "Fibroblast growth factor receptor 4 promotes progression and correlates to poor prognosis in cholangiocarcinoma," *Biochemical and Biophysical Research Communications*, 2014. 446(1): p. 54-60.
Vi, J.G.T., et al., "Identification of FGFR4-activating mutations in human rhabdomyosarcomas that promote metastasis in xenotransplanted models," *The Journal of Clinical Investigation*, 2009. 119(11): p. 3395-3407.
Streit, S., et al., "FGFR4 Arg388 allele correlates with tumour thickness and FGFR4 protein expression with survival of melanoma patients," *British Journal of Cancer*, 2006. 94(12): p. 1879-1886.
Lixia Gao., et al., "FGF19 amplification reveals an oncogenic dependency upon autocrine FGF19/FGFR4 signaling in head and neck squamous cell carcinoma," *Oncogene*, 2019. 38(13): p. 2394-2404.
Wen-Ya Zhou., "Characterization of FGFR signaling pathway as therapeutic targets for sarcoma patients," *Cancer Biol Med*, 2016. 13(2): 260-268.

COMPOUND FOR SELECTIVELY INHIBITING KINASE AND USE THEREOF

TECHNICAL FIELD

The present invention relates to compounds of formula (I) and formula (II) as selective inhibitors of fibroblast growth factor receptor kinase, the preparation methods, pharmaceutical compositions thereof and methods for inhibiting kinase activity using said compounds and compositions, as well as their medical uses.

BACKGROUND ART

Fibroblast growth factor (FGF) is a family of intracellular polypeptides comprising 22 structurally similar members, 150-300 amino acid residues. It is widely distributed in mammalian bodies, promotes cell proliferation, migration, differentiation and plays an important role in physiological activities such as embryonic development, wound repair, hematopoiesis, angiogenesis, metabolism, etc. (Itoh, N.; Ornitz, D. M. Fibroblast growth factors: From molecular evolution to roles in development, metabolism and disease. J. Biochem. 2011, 149, 121-130). Many studies have confirmed that abnormalities in the FGF family are associated with the occurrence of malignant tumors such as leukemia, sarcoma, pancreatic cancer, bladder cancer, colon cancer, breast cancer and prostate cancer.

FGF exerts its physiologically active function by binding to its specific receptor (FGFR). Mammalian FGFR includes four receptors FGFR1-4 and belongs to receptor tyrosine kinase receptor. After binding to FGF, homodimerization occurs in the transmembrane receptor, the intracellular kinase domain is phosphorylated and thus activated, and then the intracellular downstream MAPK or PI3K/AKT signaling pathway is activated and multiple signaling cascades are then activated (Lin, B. C., Desnoyers, L. R. FGF19 and cancer. Adv. Exp. Med. Biol. 2012, 728:183-94; Powers, C. J. et al., Endocr. Relat. Cancer, 2000, 7: 165-197).

FGF19 is an important metabolic regulator involved in bile synthesis, glycogen synthesis, gluconeogenesis, and protein synthesis, etc. Under normal physiological conditions, bile acids secreted into the small intestine activate the farnesoid X receptor (FXR), which stimulates the expression and secretion of FGF19 from the ileum. The natural receptor for FGF19 is FGFR4, which has high levels of expression in the liver. After FGFR4 binds to FGF19, under the action of co-factor β-Klotho (KLB), dimerization occurs and the intracellular kinase domain is autophosphorylated and then activated, and the effect of regulating physiological function is exerted by downstream cascade signals.

The human FGF19 gene is located at 11q13.1. The study found that FGF19 gene is amplified in some patients with hepatocellular carcinoma and is associated with tumor development. Another study found that ~25% of liver cancer patients have elevated expression of FGF19 protein in tumor tissues. FGFR4 also has overexpression in a variety of cancers, such as liver cancer (Ho, H. K. et al., Journal of Hepatology, 2009, 50: 118-127; Sawey, E. T. et al., Cancer Cell, 2011, 19:347-358), gastric cancer (Ye, Y. W. et al., Cancer, 2011, 117:5304-5313; Ye, Y. et al., Ann. Surg. Oncol. 2010, 17:3354-3361), pancreatic cancer (Leung, H. Y. et al., Int. J. Cancer, 1994, 59:667-675), renal cell carcinoma (Takahashi, A. et al., Biochem. Biophys. Res. Commun. 1999, 257:855-859), rhabdomyosarcoma (Taylor VI, J. G. et al., J. Clin. Invest. Doi:1o.1172/JCI39703), cholangiocarcinoma (Xu, Y.-F. et al., Biochem. Biophys. Res. Commun. 2014, 446: 54-60), colon cancer (Barderas, R. et al., J. Proteomics, 2012, 75:4647-4655; Peláez-Garcia, A., PLos ONE, 2012, 8(5): e63695), prostate cancer (Xu, B. et al., BMC cancer 2011, 11:84), ovarian cancer (Zaid, T. M. et al., Clin. Cancer Res. 2013, 19(4): 809-820) and the like. Therefore, abnormal FGF19/FGFR4 signaling pathway may be involved in the initiation and progression of various human cancers.

Given the role of the FGF/FGFR signaling pathway in tumor initiation and progression, several FGFR inhibitors have been in clinical research. Non-selective FGFR inhibitors cause side effects such as hyperphosphatemia and ectopic calcification. Selective FGFR4 inhibitors are safer for tumor patients with abnormal FGF19/FGFR4 signaling pathways.

The study found that PD173074 is a small molecule inhibitor of FGFR4, which can inhibit the growth of rhabdomyosarcoma cells and has antitumor activity in vivo (Crose, L. E. S. et al., Clin. Cancer Res. 2012, 18(14):1-11). Desnoyers et al. found that FGF19 monoclonal antibody can selectively block the interaction between FGF19 and FGFR4, which can inhibit the growth of human colon cancer xenografts in nude mice and effectively prevent FGF19 transgenic mice from suffering from liver cancer (Desnoyers, L. R. et al., Oncogene, 2008, 27:85-97). Sawey et al. found that FGF19 monoclonal antibody can significantly inhibit the growth of human liver cancer xenografts (Sawey, E. T. et al., Cancer Cell, 2011, 19, 347-358). Ho et al. found that small molecule inhibitors of FGFR4 can induce apoptosis of breast cancer cells and inhibit cancer cell migration (Ho, H. K. et al. Current Medicinal Chemistry, 2013, 20:1203-1217). Selective FGFR4 small molecule inhibitor BLU9931 can inhibit the proliferation of liver cancer cells and inhibit the growth of human liver cancer xenografts in a dose-dependent manner (Hagel, M. et al., Cancer Discov. 2015, 5(4): 1-14). These studies show that selective inhibition of FGFR4 and blocking of FGF19/FGFR4 signaling pathway can inhibit tumor growth and provide an effective target for molecular targeted therapy of tumors.

Although individual compounds having an effect of inhibiting FGFR4 kinase have been disclosed so far, there is still a need to develop new compounds having better therapeutic effects and safety windows, and the present invention designs compounds having the structures of the general formulas (I) and (II), and compounds with such structures have been found to exhibit superior efficacy and safety windows and have significant and important application value.

SUMMARY OF THE INVENTION

The present invention relates to novel FGFR4 selective small molecule inhibitor compounds and pharmaceutically acceptable salts thereof. The present invention also relates to compositions of these compounds, alone or in combination with at least one additional therapeutic agent and optionally a pharmaceutically acceptable carrier. The present invention further relates to the use or usage method of these compounds, alone or in combination with at least one additional therapeutic agent for the prevention or treatment of a disease mediated by FGFR4 or FGF19.

The present invention discloses a compound of formula (I), a stereoisomer, a tautomer or a pharmaceutically acceptable salt thereof,

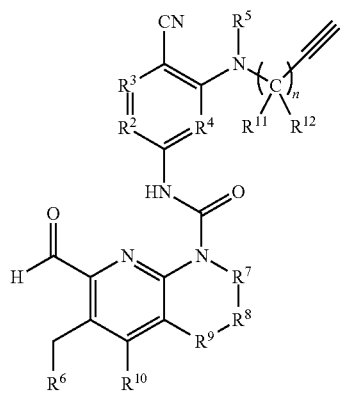

(I)

wherein, $R^2$, $R^3$ and $R^4$ are independently N or $C(R^X)$;

$R^5$ is selected from the group consisting of hydrogen, halogen, cyano, amino, amido, hydroxyl, ester, acyl, acyloxy, sulfonyl, sulfinyl, alkyl, alkoxyl, aryl, cycloalkyl, hetero aryl, heterocyclyl and heterocyclylalkyl;

$R^6$ is selected from the group consisting of hydrogen, halogen, cyano, amino, amido, hydroxyl, ester, acyl, acyloxy, sulfonyl, sulfinyl, alkyl, alkoxyl, aryl, cycloalkyl, hetero aryl, heterocyclyl and heterocyclylalkyl;

$R^7$, $R^8$ and $R^9$ are independently N or $C(R^X)$;

$R^{10}$, $R^{11}$ and $R^{12}$ are independently hydrogen, halogen, cyano, amino, hydroxyl, alkyl, alkoxyl, aryl, cycloalkyl, heteroaryl, or the two substituents $R^{11}$ and $R^{12}$ are cyclized into a cyclic group, $R^X$ is independently hydrogen, halogen, cyano, amino, amido, hydroxyl, ester, acyl, acyloxy, sulfonyl, sulfinyl, alkyl, alkoxyl, aryl, cycloalkyl, heteroaryl or heterocyclyl, n=1, 2, 3, 4, 5.

The compound of formula (I) of the present invention, the stereoisomer, the tautomer or the pharmaceutically acceptable salt thereof, comprises a compound of general formula (II),

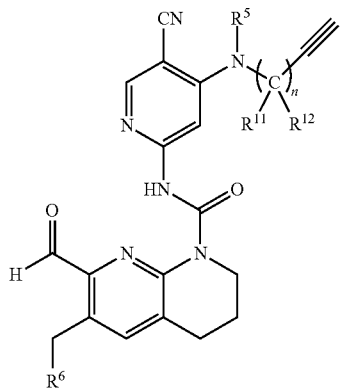

(II)

wherein $R^5$ is hydrogen, alkyl, alkoxyl, aryl, cycloalkyl, heteroaryl, heterocyclyl, heterocyclylalkyl, $R^{11}$ and $R^{12}$ are independently hydrogen, halogen, cyano, amino, hydroxyl, alkyl, alkoxyl, aryl, cycloalkyl, heteroaryl, or the two substituents $R^{11}$ and $R^{12}$ are cyclized into a cyclic group, n=1, 2, 3, 4, 5, $R^6$ is selected from the following structures:

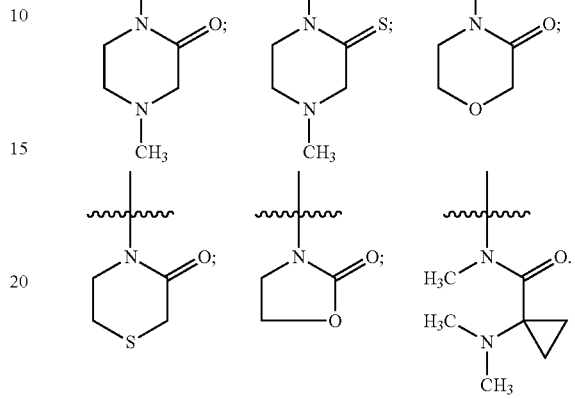

The compound of formula (II) of the present invention, wherein the structure

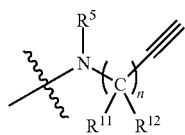

is selected from the following structures:

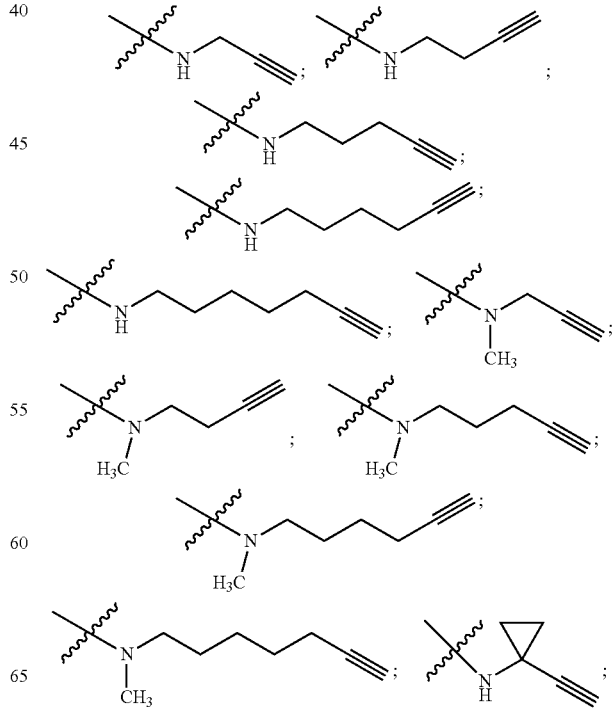

5
-continued
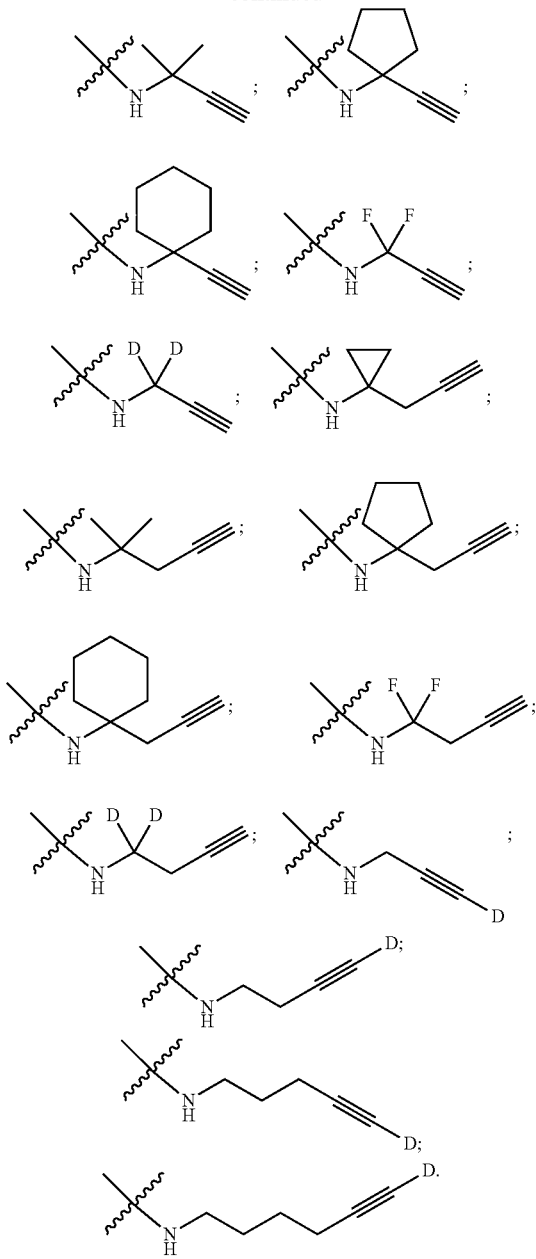
The compounds of formula (I) and formula (II) of the present invention, their stereoisomers, tautomers or pharmaceutically acceptable salts, are preferably the following compounds:
6
-continued
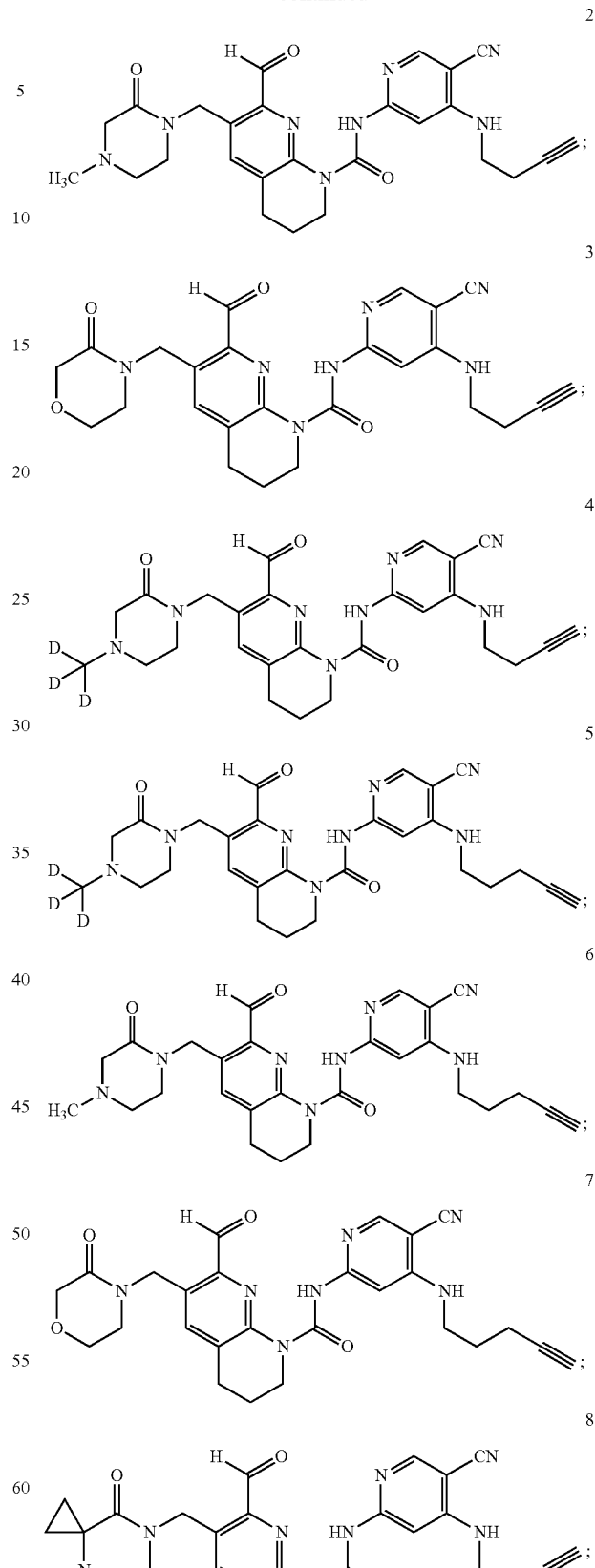

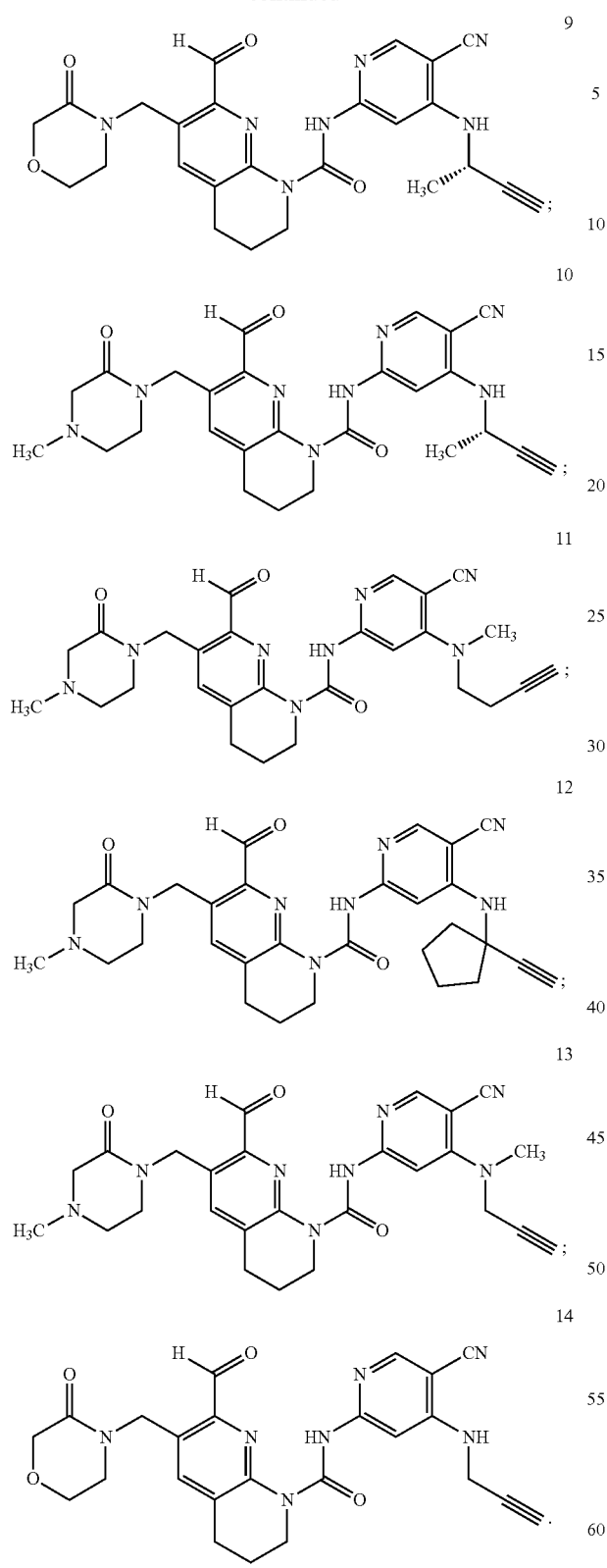
The method for preparing the compound of the present invention, the stereoisomer, the tautomer or the pharmaceutically acceptable salt thereof, comprises the following steps:
wherein, $R^5$, $R^6$, $R^{11}$, $R^{12}$ and n are as defined above; $R^y$ and $R^z$ are selected from C1-C6 alkyl groups. Wherein the alkali is selected from the group consisting of lithium bis(trimethylsilyl)amide, sodium bis(trimethylsilyl)amide and potassium bis(trimethylsilyl)amide, preferably lithium bis(trimethylsilyl)amide.

The present invention provides a pharmaceutical composition comprising a therapeutically effective amount of the compound, or the stereoisomer, the tautomer or the pharmaceutically acceptable salt thereof of any one of the present invention and the pharmaceutically acceptable carrier.

Further provided is use of the compound of any one of the present invention, the stereoisomer, tautomer or pharmaceutically acceptable salt thereof, as a selective inhibitor of FGFR4 kinase, for the preparation of a medicament or pharmaceutical composition for treating a disease mediated by FGFR4 or FGF19.

Further provided is use of the compound of any one of the present invention, the stereoisomer, the tautomer or the pharmaceutically acceptable salt thereof and the pharmaceutical composition of the present invention for the preparation of a medicament for treating cancer.

Further provided is the medicament or pharmaceutical composition of the present invention, which is used for the treatment of various cancers.

According to the present invention, the various cancers treated include: liver cancer, lung cancer, esophageal cancer, gastric cancer, renal cell carcinoma, sarcoma, cholangiocarcinoma, colon cancer, prostate cancer, ovarian cancer and breast cancer.

DETAILED DESCRIPTION OF THE INVENTION

The term "hydrogen" as used herein refers to —H.

The term "halogen" as used herein refers to —F, —Cl, —Br and —I.

The term "fluorine" as used herein refers to —F.

The term "chlorine" as used herein refers to —Cl.

The term "bromine" as used herein refers to —Br.

The term "iodine" as used herein refers to —I.

The term "cyano" as used herein refers to —CN.

The term "amino" as used herein refers to —NH$_2$.

The term "hydroxyl" as used herein refers to —OH.

The term "aryl" as used herein refers to a six- to ten-membered all-carbon monocyclic or fused polycyclic (i.e., a ring that shares a pair of adjacent carbon atoms) group, and polycyclic (i.e., a ring that has a pair of adjacent carbon atoms) group having conjugated π-electron system. The aryl group can be covalently attached to a defined chemical structure at any carbon atom that results in a stable structure. The aryl groups described herein can be optionally substituted with one or more of the following substituents: fluorine, chlorine, bromine, iodine, cyano, nitro, hydroxyl, carboxyl, amino, alkyl, alkoxyl, acyl, amido, ester, amine, sulfonyl, sulfinyl, cycloalkyl, cycloalkenyl, heterocycloalkyl, alkenyl, alkynyl and cycloalkoxyl.

The term "heteroaryl" as used herein refers to an aromatic group consisting of 5 to 10 atoms and containing at least one heteroatom selected from N, O or S. The term may have a single ring (non-limiting examples include furan, thiophene, imidazole, pyrazole, pyridine, pyrazine, oxazole, thiazole, etc.) or multiple fused rings (non-limiting examples include benzothiophene, benzofuran, indole, isoindole, etc.), wherein the fused ring may or may not be an aromatic group containing a heteroatom, assuming that the point of attachment is atoms through an aromatic heteroaryl group. The heteroaryl groups described herein can be optionally substituted with one or more of the following substituents: fluorine, chlorine, bromine, iodine, cyano, nitro, hydroxyl, amino, alkyl, alkoxyl, acyl, acyloxy, amido, ester, amine, sulfonyl, sulfinyl, cycloalkyl, cycloalkenyl, heterocycloalkyl, alkenyl, alkynyl and cycloalkoxyl.

The term "cycloalkyl" as used herein refers to a monocyclic or polycyclic (including fused ring, bridged ring and spiro ring systems) cyclic alkyl group of 3 to 10 carbon atoms. Non-limiting examples of cycloalkyl groups include cyclopropyl, cyclobutyl, cyclopentyl, cyclohexyl, and the like. The cycloalkyl groups described herein can be optionally substituted with one or more of the following substituents: fluorine, chlorine, bromine, iodine, cyano, nitro, hydroxyl, carboxyl, amino, alkyl, oxo, alkoxyl, acyl, acyloxy, amido, ester, amine, cycloalkyl, cycloalkenyl, heterocycloalkyl, alkenyl, alkenyloxy, alkynyl, cycloalkoxy, aryl or heteroaryl.

The term "heterocyclyl" refers to substituted or unsubstituted, saturated or unsaturated aromatic ring and non-aromatic ring containing at least 1 to 5 heteroatoms selected from N, O or S. The aromatic ring and non-aromatic ring can be a three- to ten-membered monocyclic ring, a four- to twenty-membered spiro ring, fused ring or bridged ring. The optionally substituted N, S in the heterocyclyl ring can be oxidized to various oxidation states. A three- to twelve-membered heterocyclic ring is preferred. Non-limiting examples include oxacyclopropyl, oxacyclobutyl, oxacyclopentyl, oxacyclohexyl, oxacyclohexyl, oxacyclooctyl, azacyclopropyl, azacyclobutyl, azacyclopentyl, azacyclohexyl, azacyclopropenyl, 1,3-dioxocyclopentyl, 1,4-dioxocyclopentyl, 1,3-dioxocyclopentyl, 1,3-dioxacyclohexyl, 1,3-dithiocyclohexyl, azacycloheptenyl, morpholinyl, piperazinyl, pyridyl, furyl, thienyl, pyrrolyl, pyranyl, N-alkylpyrrolyl, pyrimidinyl, pyrazinyl, pyridazinyl, imidazolyl, piperidinyl, thiomorpholinyl, dihydropyranyl, thiadiazolyl, oxazolyl, oxadiazolyl, pyrazolyl, 1,4-dioxacyclohexadienyl or the like. Non-limiting examples include the following structures:

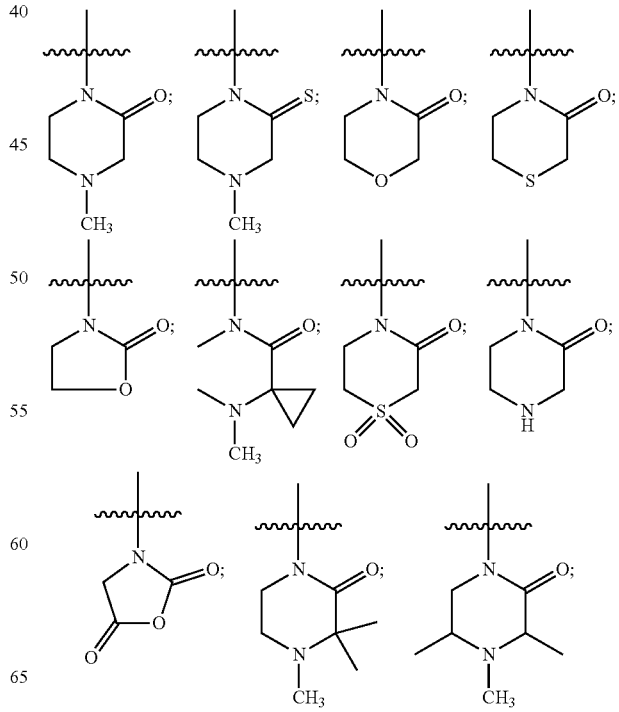

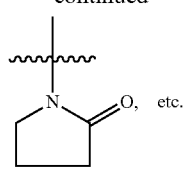

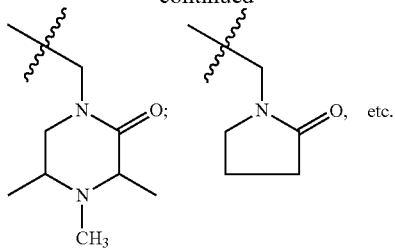

The term "heterocycloalkyl" as used herein refers to a non-aromatic cycloalkyl group containing at least one heteroatom selected from O, N and S and optionally containing one or more double or triple bonds. The heterocycloalkyl group as a whole can have from 3 to 10 ring atoms. The heterocycloalkyl group can be covalently attached to a defined chemical structure at any heteroatom or carbon atom that results in a stable structure. Non-limiting examples of heterocycloalkyl groups include: pyrrolinyl, piperidinyl, piperazinyl, tetrahydrofuranyl, tetrahydropyranyl, morpholinyl, pyranyl and the like. One or more N or S atoms on the heterocycloalkyl group can be oxidized (such as morpholine N-oxide, thiomorpholine S-oxide, thiomorpholine S, S-dioxide). The heterocycloalkyl group can also contain one or more oxo groups such as phthalimido, piperidinone, oxazolidinone, 2,4(1H,3H)-dioxo-pyrimidinyl, pyridine-2 (1H)-keto group and the like. The heterocycloalkyl group described herein can be optionally substituted with one or more of the following substituents: fluorine, chlorine, bromine, iodine, cyano, nitro, hydroxyl, carboxyl, amino, alkyl, alkoxyl, oxo, acyl, acyloxy, amido, ester, amine, cycloalkyl, cycloalkenyl, heterocycloalkyl, alkenyl, alkenyloxy, alkynyl, cycloalkoxy, aryl or heteroaryl. Non-limiting examples include the following structure:

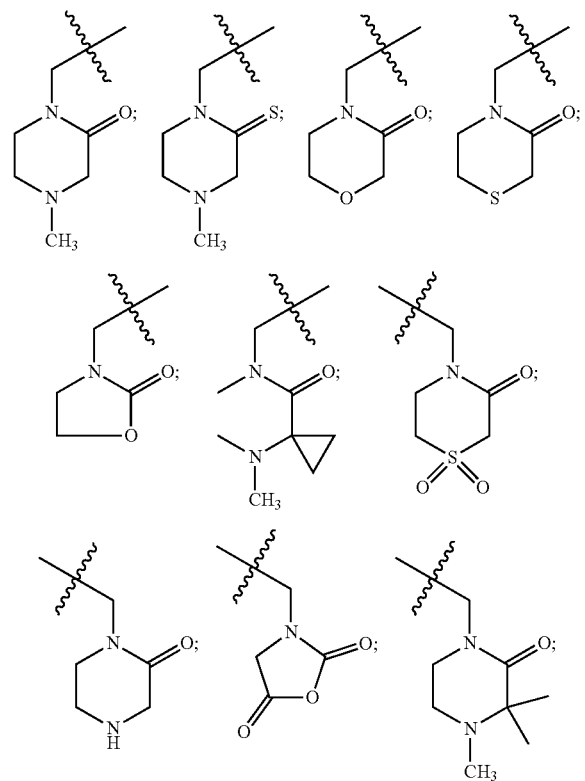

The term "alkenyl" as used herein refers to an alkenyl group having from 2 to 8 carbon atoms and having at least one alkenyl unsaturated site. Non-limiting examples of alkenyl groups include ethenyl, propenyl, allyl, isopropenyl, butenyl, isobutenyl, and the like. The alkenyl group described herein can be optionally substituted with one or more of the following substituents: fluorine, chlorine, bromine, iodine, cyano, nitro, hydroxyl, carboxyl, amino, alkyl, alkoxyl, oxo, acyl, acyloxy, amido, ester, amine, cycloalkyl, cycloalkenyl, heterocycloalkyl, alkenyl, alkenyloxy, alkynyl, alkynyloxy, cycloalkoxy, aryl or heteroaryl.

The term "alkyl" as used herein refers to a saturated aliphatic hydrocarbyl group having from 1 to 10 carbon atoms, and the term includes both straight chain and branched chain hydrocarbon groups. Non-limiting examples of alkyl groups include methyl, ethyl, n-propyl, isopropyl, n-butyl, isobutyl, sec-butyl, tert-butyl, n-pentyl, neopentyl, n-hexyl, and the like. The alkyl group described herein can be optionally substituted with one or more of the following substituents: fluorine, chlorine, bromine, iodine, cyano, nitro, hydroxyl, carboxyl, amino, alkyl, alkoxyl, acyl, acyloxy, oxo, amido, ester, amine, cycloalkyl, cycloalkenyl, heterocycloalkyl, alkenyl, alkenyloxy, alkynyl, cycloalkoxy, heterocycloalkyloxy, aryloxy, heteroaryloxy, aryl or heteroaryl.

The term "alkoxyl" as used herein refers to an alkyl group attached to the remainder of the molecule through an oxygen atom (—O-alkyl), wherein the alkyl group is as defined herein. Non-limiting examples of alkoxy groups include methoxy, ethoxy, trifluoromethoxy, difluoromethoxy, n-propoxy, isopropoxy, n-butoxy, tert-butoxy, n-pentyloxy and the like.

The term "amido" as used herein refers to —NR$^{30}$—C(O)-alkyl, —NR$^{30}$—C(O)-cycloalkyl, —NR$^{30}$—C(O)-cycloalkenyl, —NR$^{30}$—C(O)-aryl, —NR$^{30}$—C(O)-heteroaryl and —NR$^{30}$—C(O)-heterocycloalkyl, wherein R$^{30}$ is hydrogen, cycloalkyl, cycloalkenyl, aryl, heteroaryl, heterocycloalkyl and alkyl. Wherein, the groups such as hydrogen, cycloalkyl, cycloalkenyl, aryl, heteroaryl, heterocycloalkyl and alkyl are as defined herein.

The term "acyl" as used herein refers to H—C(O)—, R$^{31}$R$^{32}$N—C(O)—, alkyl-C(O)—, cycloalkyl-C(O)—, cycloalkenyl-C(O)—, heterocycloalkyl-C(O)—, aryl-C(O)— and heteroaryl-C(O)—, wherein the R$^{31}$ and R$^{32}$ are each independently selected from the group consisting of hydrogen, hydroxyl, alkyl, heterocycloalkyl, aryl, heteroaryl, sulfonyl, sulfinyl, cycloalkenyl, acyl or cycloalkyl. Wherein, the groups such as hydrogen, hydroxyl, alkyl, heterocycloalkyl, aryl, heteroaryl, sulfonyl, sulfinyl, cycloalkenyl, acyl and cycloalkyl are as defined herein.

The term "sulfonyl" as used herein refers to R$^{33}$R$^{34}$N—S(O)$_2$—, cycloalkyl-S(O)$_2$—, cycloalkenyl-S(O)$_2$—, aryl-S(O)$_2$—, hetero aryl-S (O)$_2$—, heterocycloalkyl-S(O)$_2$— and alkyl-S(O)$_2$—, wherein the R$^{33}$ and R$^{34}$ are each independently selected from the group consisting of hydrogen, hydroxyl, alkyl, heterocycloalkyl, aryl, heteroaryl, sulfonyl, sulfinyl, cycloalkenyl, acyl or cycloalkyl. Wherein, the groups such as hydrogen, hydroxyl, alkyl, heterocycloalkyl, aryl, heteroaryl, sulfonyl, sulfinyl, cycloalkenyl, acyl and cycloalkyl are as defined herein.

The term "sulfinyl" as used herein refers to $R^{35}R^{36}N$—S(O)—, cycloalkyl-S(O)—, cycloalkenyl-S(O)—, aryl-S(O)—, heteroaryl-S(O)—, heterocycloalkyl-S(O)— or alkyl-S(O)—, wherein the $R^{35}$ and $R^{36}$ are each independently selected from the group consisting of hydrogen, hydroxyl, alkyl, heterocycloalkyl, aryl, heteroaryl, sulfonyl, sulfinyl, cycloalkenyl, acyl or cycloalkyl. Wherein the groups such as hydrogen, hydroxyl, alkyl, heterocycloalkyl, aryl, heteroaryl, sulfonyl, sulfinyl, cycloalkenyl, acyl and cycloalkyl are as defined herein.

The term "acyloxy" as used herein refers to —O—C(O)-alkyl, —O—C(O)-cycloalkyl, —O—C(O)-cycloalkenyl, —O—C(O)-aryl, —O—C(O)-heteroaryl and —O—C(O)-heterocycloalkyl, wherein the groups such as alkyl, cycloalkyl, cycloalkenyl, aryl, heteroaryl and heterocycloalkyl are as defined herein.

The term "ester" as used herein refers to alkyl-O—C(O)—, cycloalkyl-O—C(O)—, cycloalkenyl-O—C(O)—, heterocycloalkyl-O—C(O)—, aryl-O—C(O)— and heteroaryl-O—C(O)—, wherein the groups such as alkyl, cycloalkyl, cycloalkenyl, heterocycloalkyl, aryl and heteroaryl are as defined herein.

The term "optional" or "optionally" means that the subsequently described event or circumstance may, but does not necessarily, occur, and this description includes instances in which the event or circumstance occurs and it does not occur.

The term "optionally substituted with . . . " means that the structure is unsubstituted or substituted with one or more substituents of the present invention. The term "substitution" as used herein means the single or multiple substitution of any group by a designated substituent to the extent that such single or multiple substitution (including multiple substitutions in the same moiety) is chemically permissible, wherein each substituent can be located at any available position on the group and can be attached through any available atom on the substituent. "Any available position" refers to any position on the group, which is chemically obtainable by methods known in the art or as taught herein and does not create molecules that are excessively unstable. When there are two or more substituents on any group, each substituent is defined independently of any other substituent and thus may be the same or different.

In various parts of the specification, substituents of the compounds of the present invention are disclosed in the form of groups or ranges. This specifically means that the present invention encompasses each of the members of such groups or ranges or subgroups of each of the members. The term "$C_{1-6}$ alkyl" specifically means that methyl, ethyl, $C_3$ alkyl, $C_4$ alkyl, $C_5$ alkyl and $C_6$ alkyl are disclosed separately.

The term "compounds of the present invention" (unless otherwise specifically indicated) as used herein refers to compounds of formula (I) and formula (II) and all their pure and mixed stereoisomers, geometric isomers, tautomers, solvates, prodrugs and isotopically labeled compounds and any pharmaceutically acceptable salts. The solvate of the compound of the present invention means a compound or a salt thereof, such as a hydrate, an ethylate, a methylate, an acetonate or the like, in combination with a stoichiometric and non-stoichiometric solvent. The compound can also be present in one or more crystalline states, i.e., as a co-crystal, a polymorph, or it can be present as an amorphous solid. All such forms are covered by the claims.

The term "pharmaceutically acceptable" means that the substance or composition must be chemically and/or toxicologically compatible with the other ingredients that make up the formulation and/or the mammal treated by it.

The term "stereoisomer" as used herein refers to a compound which has a different chirality and one or more stereocenters, including the enantiomer and diastereomer.

The term "tautomer" as used herein refers to structural isomer having a different energy that can cross the low energy barrier and thereby transform each other. One example is proton tautomers including interconversion by proton transfer, such as enol-keto tautomers and imine-enamine tautomers, or a tautomeric form of a heteroaryl group containing a ring atom attached to ring-NH-moiety and ring=N-moiety, such as pyrazole, imidazole, benzimidazole, triazole and tetrazole. Valence tautomers include some bond-forming electron recombination for interconversion.

The term "prodrug" as used herein refers to any derivative of the compound of the present invention that is capable of providing, directly or indirectly, the compound of the present invention, an active metabolite or residue thereof, when administered to a subject. Particularly preferred are those derivatives or prodrugs which can increase the bioavailability of the compound of the present invention, increase metabolic stability and tissue targeting.

The compound of the present invention can be used in the form of a salt such as a "pharmaceutically acceptable salt" derived from an inorganic or organic acid. These include, but are not limited to, the following substances: acetate, adipate, alginate, citrate, aspartate, benzoate, besylate, ethanesulfonate, disulfate, butyrate, camphorate, camphorsulfonate, digluconate, cyclopentane propionate, lauryl sulfate, ethanesulfonate, glucose heptanoate, glycerol phosphate, hemisulphate, heptanoate, hexanoate, fumarate, hydrochloride, hydrobromide, hydroiodide, 2-hydroxy-ethanesulfonate, lactate, maleate, methanesulfonate, ethanesulfonate, hydrochloride, 2-naphthalene sulfonate, oxalate, pectate ester, sulfate, 3-phenylpropionate, picrate, trimethylacetate, propionate, succinate, tartrate, thiocyanate, p-toluenesulfonate and decanoate. In addition, basic nitrogen-containing groups can be quaternized with the following reagents to form quaternary ammonium salts: lower alkyl halide, including chloride, bromide and iodide of methyl, ethyl, propyl and butyl groups; dialkylsulfate, including dimethylsulfate, diethylsulfate, dibutylsulfate and dipentylsulfate; long chain halide, including chloride, bromide and iodide of decyl, lauryl, myristyl, and stearyl groups; aralkyl halide, such as bromide of benzyl and phenethyl groups.

The present invention also includes isotopically labeled compounds of the present invention, which are identical to those disclosed above in structure, but in which one or more atoms are replaced by an atom having the same number of protons but a different number of neutrons. Examples of the isotope incorporating into the compound of the present invention include isotopes of hydrogen, carbon, nitrogen, oxygen, sulfur, fluorine, chlorine and iodine, such as $^2H$, $^3H$, $^{13}C$, $^{14}C$, $^{15}N$, $^{18}O$, $^{17}O$, $^{35}S$, $^{18}F$, $^{36}Cl$ and $^{131}I$, etc. The compound of the present invention, the stereoisomer, tautomer or pharmaceutically acceptable salt thereof, and the compound of the above forms containing the above isotopes and/or isotopes of other atoms are within the scope of the present invention. Certain isotopically labeled compounds of the present invention, such as those labeled with $^3H$ or $^{14}$C, can be used in drug tissue distribution assays, and therefore, these $^3$H or $^{14}$C isotopes are particularly preferred because of their ease of preparation and detection. In addition, certain compounds of the present invention that are replaced by heavier isotopes such as $^2$H have certain therapeutic advantages due to better metabolic stability, such as increased in vivo half-life and lower doses, etc., therefore, $^2$H is also preferred in some cases.

The compound of the present invention has a FGFR4 selective inhibitory action and is useful for the preparation of a medicament or pharmaceutical composition for human or veterinary use for the treatment of diseases associated with FGFR4 or FGF19 mediated diseases such as cancer. In particular, the compound can be used to treat cancer in humans or animals, including liver cancer, gastric cancer, pancreatic cancer, renal cell carcinoma, sarcoma, cholangiocarcinoma, colon cancer, prostate cancer, ovarian cancer, breast cancer, etc.

DETAILED DESCRIPTION OF THE INVENTION

Figure 1:
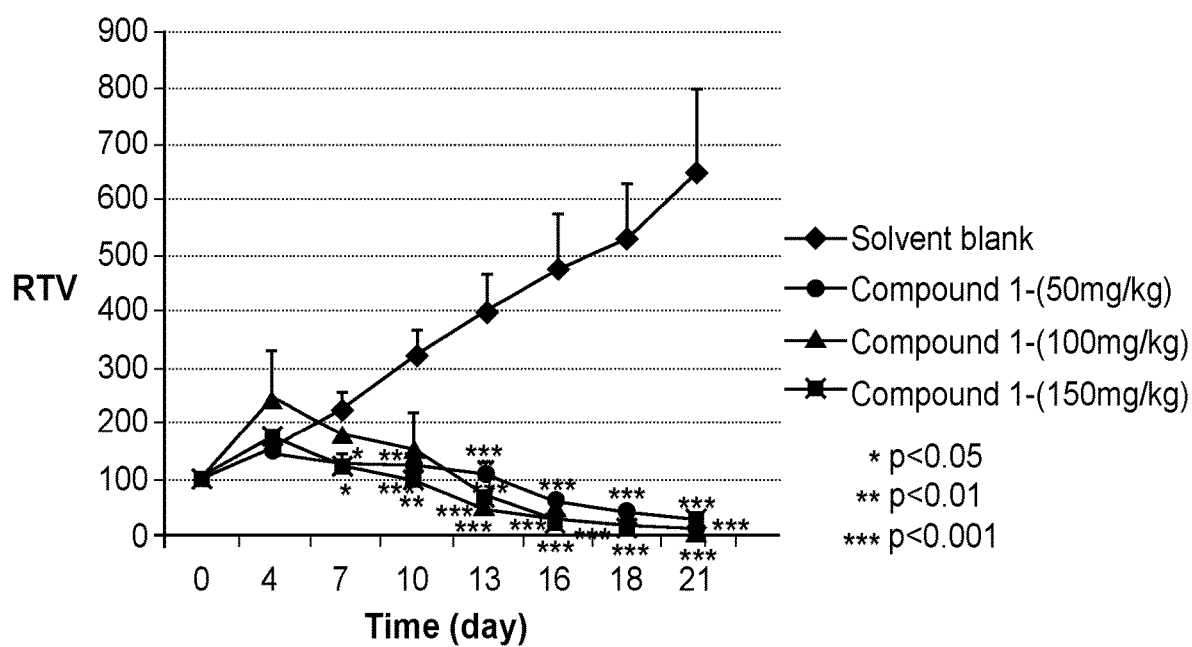
FIG. 1 shows the results of in vivo efficacy test using HEP3B cells in a hepatocellular carcinoma model. Compound 1 and solvent blank control were orally administered by intragastric gavage, and relative tumor volume during the experimental period was measured.

Throughout the present application, various examples of the compound and method of the present invention are referred to herein. The various examples described are intended to provide a number of illustrative examples and should not be construed as a description of alternatives. It should be noted that the examples (including various methods and parameters) discussed herein are merely illustrative of the present invention and are not intended to limit the protection scope of the protection invention by any means. For the purpose of describing the present invention, specific examples are set forth below. However, it is to be understood that the present invention is not limited to these examples, and the following examples are merely intended to provide a method of practicing the present invention and are not intended to limit the scope of the present invention by any means.

The compounds of the general formula of the present invention are prepared according to the following preparation method:

The preparation method of the compound of the general formula (I) is summarized as follows:

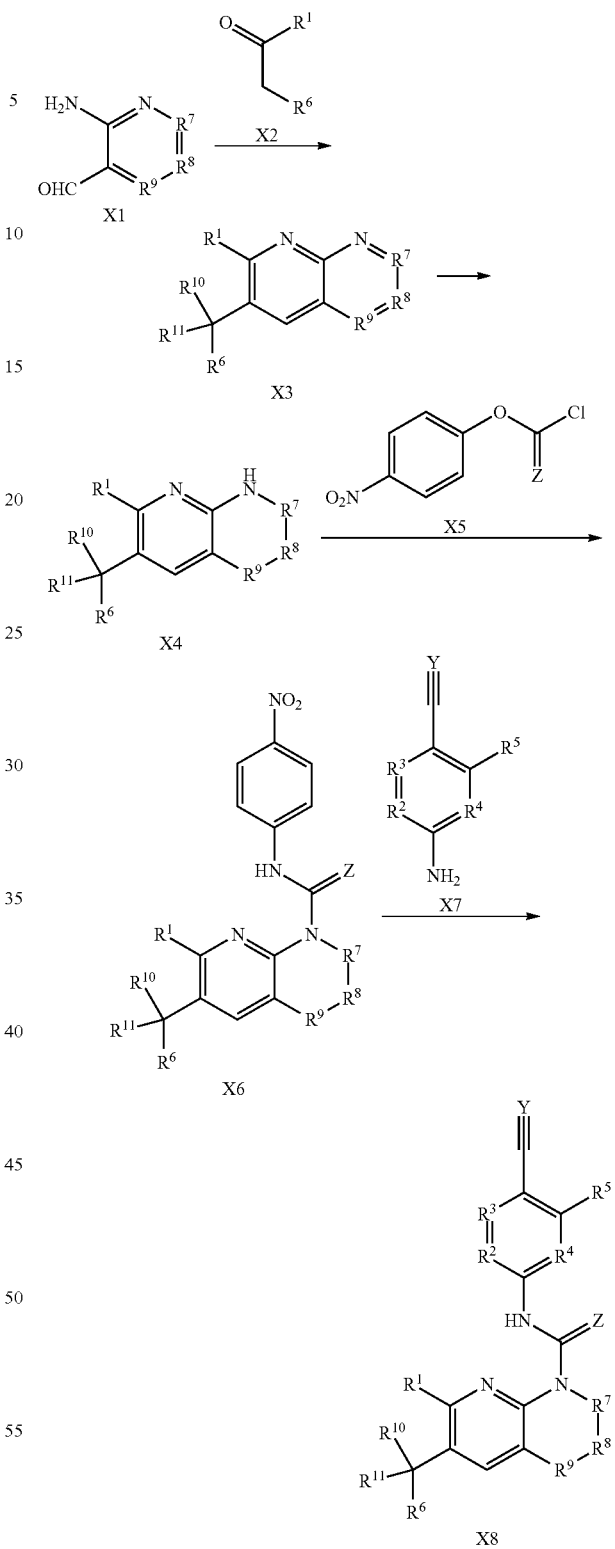

First, the starting material X1 is coupled with the starting material X2 to obtain the compound X3, the compound X3 is reduced to obtain the compound X4, the compound X4 is coupled with the compound X5 to obtain the compound X6, and the compound X6 is exchanged with the compound X7 to obtain the final general formula compound X8.

More specifically, the preparation method of the compound of the general formula (II) is summarized as follows:

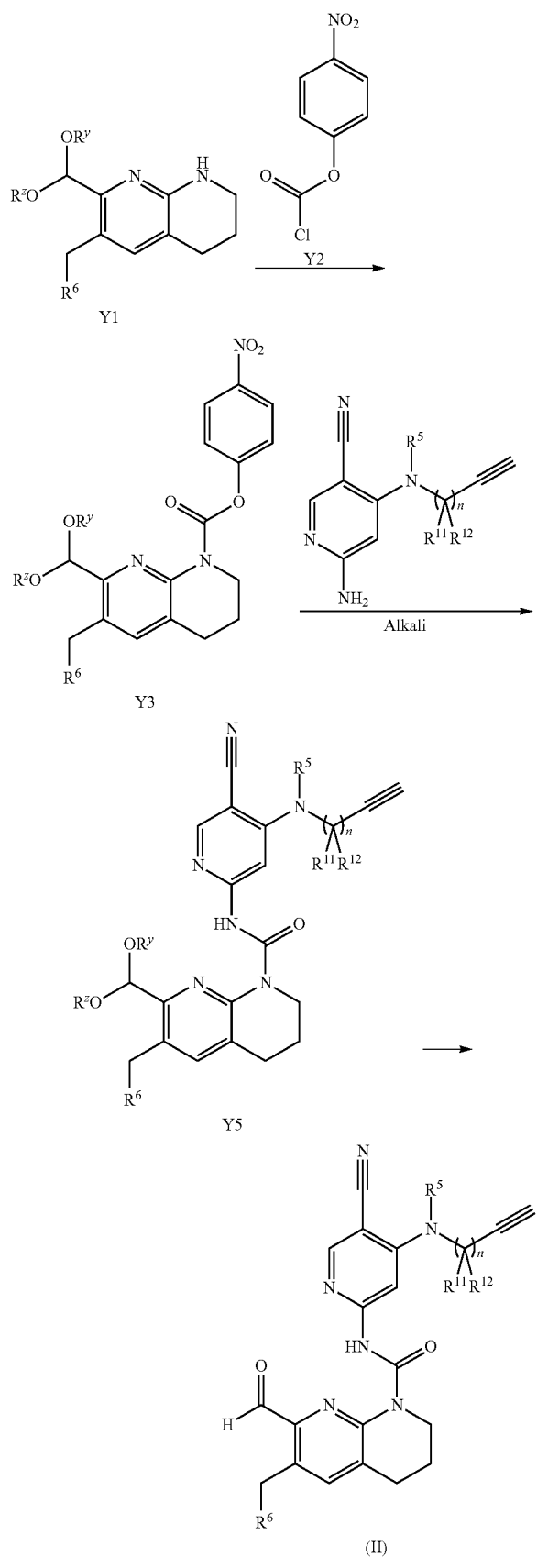

wherein, $R^5$, $R^6$, $R^{11}$, $R^{12}$ and n are as defined in claim 2; $R^y$ and $R^z$ are selected from C1-C6 alkyl groups, or $R^y$ and $R^z$ are linked to form a five- to seven-membered heterocyclic structure, comprising the following steps:

Step 1, in a certain solvent, at a certain temperature, the compounds Y1 and Y2 are coupled under the action of an alkali to form the compound Y3;

Step 2, in a certain solvent, at a certain temperature, the compounds Y3 and Y4 are reacted under the action of an alkali to obtain the compound Y5;

Step 3, in a certain solvent, at a certain temperature, the compound Y5 is deprotected by a deprotecting reagent to obtain the compound (II);

wherein, in step 1, the solvent is one or more selected from the group consisting of tetrahydrofuran, dioxane, dichloromethane, chloroform, tetrachloromethane, acetonitrile, dichloroethane and ethyl acetate, and the solvent is preferably dichloromethane, chloroform; the temperature is selected from −30 to 80° C., preferably from −10 to 20° C.; the alkali used is selected from the group consisting of triethylamine, N,N'-dimethylpropylamine, N,N'-diisopropylethylamine, aqueous solution of methylamine, preferably N,N'-diisopropylethylamine;

in step 2, the solvent is one or more selected from the group consisting of tert-butyl methyl ether, diethyl ether, tetrahydrofuran, dioxane, dichloromethane, chloroform, acetonitrile and dichloroethane, the solvent is preferably tetrahydrofuran, dioxane; the temperature is selected from −50 to 80° C., preferably from −30 to 10° C., and the selected alkali is selected from the group consisting of lithium bis(trimethylsilyl)amide, sodium bis(trimethylsilyl)amide, potassium bis(trimethylsilyl)amide, preferably lithium bis(trimethylsilyl)amide;

in step 3, the solvent is one or more selected from the group consisting of tert-butyl methyl ether, diethyl ether, tetrahydrofuran, dioxane, dichloromethane, chloroform, tetrachloromethane, acetone, butanone, ethyl acetate and water; the solvent is preferably tetrahydrofuran, water, or a mixed solution of tetrahydrofuran and water; the temperature is selected from −30 to 80° C., preferably from −10 to 10° C.; the selected deprotecting reagent is an acidic substance, preferably selected from phosphoric acid, sulfuric acid, concentrated hydrochloric acid, nitric acid, citric acid, methanesulfonic acid, p-toluenesulfonic acid, more preferably selected from concentrated hydrochloric acid, sulfuric acid.

The compound provided by the present invention can be prepared by standard synthetic methods well known in the art, and the present specification provides general methods for preparing the compound of the present invention. The starting materials are usually commercially available, such as from companies such as Alfa Aesar®, Sigma-Aldrich®, TCI, J&K®, Accela Chemical, Energy Chemical, etc., or prepared by methods well known to those skilled in the art.

In the preparation of the compound of the present invention, it may be desirable to protect certain interfering functional groups of the intermediate (e.g., primary amine or secondary amine). The requirements for such protecting groups vary depending on the nature of the particular functional group and the conditions of the preparation method. Suitable amino protecting groups include acetyl, trifluoroacetyl, tert-butoxycarbonyl (Boc), benzyloxycarbonyl (Cbz), 9-fluorenylmethoxycarbonyl (Fmoc) and the like. Suitable hydroxy protecting groups include allyl, acetyl, silanyl, benzyl, trityl, p-methoxybenzyl and the like. Such protecting groups can be readily determined by those skilled in the art (see, for example, Protective Groups in Organic Synthesis, John Wiley & Sons, New York, Third Edition, 1999).

The compounds of the present invention and the corresponding preparation methods are further explained and exemplified below by way of examples and preparations. It will be appreciated that although typical or preferred reaction conditions (e.g., reaction temperature, time, molar ratio of reactants, reaction solvent and pressure, etc.) are given in the specific examples, other reaction conditions can be used by those skilled in the art. Optimum reaction conditions may vary depending on the particular reaction substrate or solvent employed, but such conditions can be determined by one of ordinary skill in the art by routine optimization.

The structures of the compounds of the following examples were characterized by nuclear magnetic resonance (NMR) and/or mass spectrometry (MS). In Bruker Ascend 400 MHz NMR spectrometer, the compound was dissolved in a suitable deuterated reagent and $^1$H-NMR analysis was performed using TMS as an internal standard at ambient temperature. The NMR chemical shift (δ) is in ppm and uses the following abbreviations: s, singlet; d, doublet; t, triplet; q, quartet; m, multiplet; brs, broad singlet. MS was determined by Waters UPLC-Vevo™ TQ MS mass spectrometer (ESI).

The reaction starting materials, intermediates and the compounds of the examples can be isolated and purified by conventional techniques such as precipitation, filtration, crystallization, evaporation, distillation and chromatography (e.g., column chromatography, TLC separation and purification, etc.).

TLC was performed on Yantai Huanghai HSGF254 thin layer chromatography silica gel plate (0.2±0.03 mm). TLC separation and purification was performed on Yantai Huanghai HSGF254 thin layer chromatography thick preparation plate (0.9-1 mm). The Yantai Huanghai HSGF254 thin layer chromatography silica gel plate and the Yantai Huanghai HSGF254 thin layer chromatography thick preparation plate were both purchased from Qingdao Ocean Chemical Plant. Column chromatography was conducted using Yantai Huanghai 300-400 mesh silica gel as a carrier and this carrier was purchased from Qingdao Ocean Chemical Plant.

The commercial solvents and reagents used in the test, unless otherwise specified, were directly used without any further purification or treatment after purchase. The reaction conditions (reaction temperature, reaction solvent, reactant molar ratio or/and reaction duration) may be different with reference to other examples or synthetic methods. In general, the progress of the reaction can be monitored by TLC, and the appropriate time is selected to terminate the reaction and then conduct post-processing. The purification conditions of the compound may also vary. Generally, a suitable column chromatography eluent is selected according to the $R_f$ value of TLC, or the corresponding compound is isolated and purified by preparative TLC.

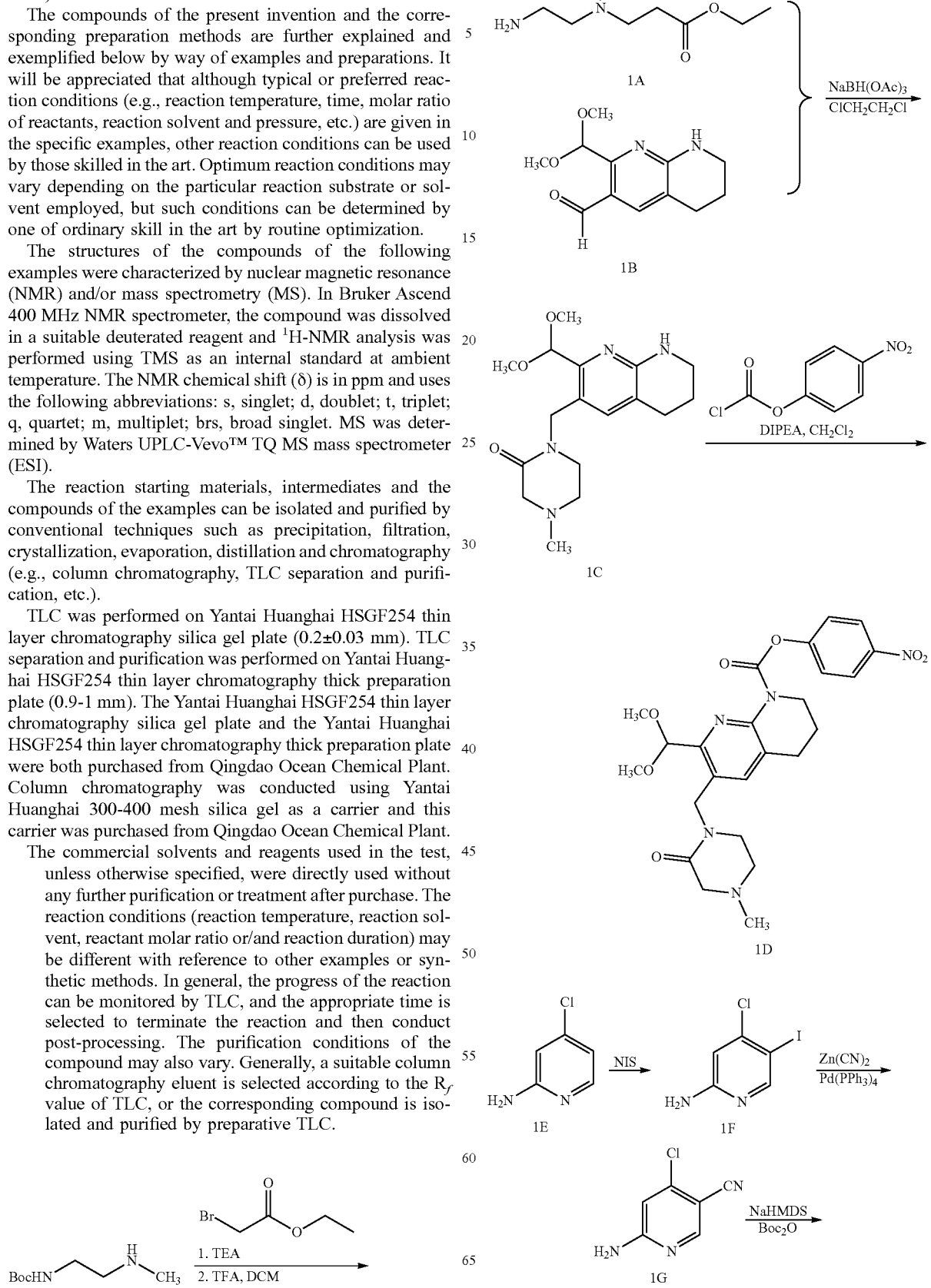

-continued

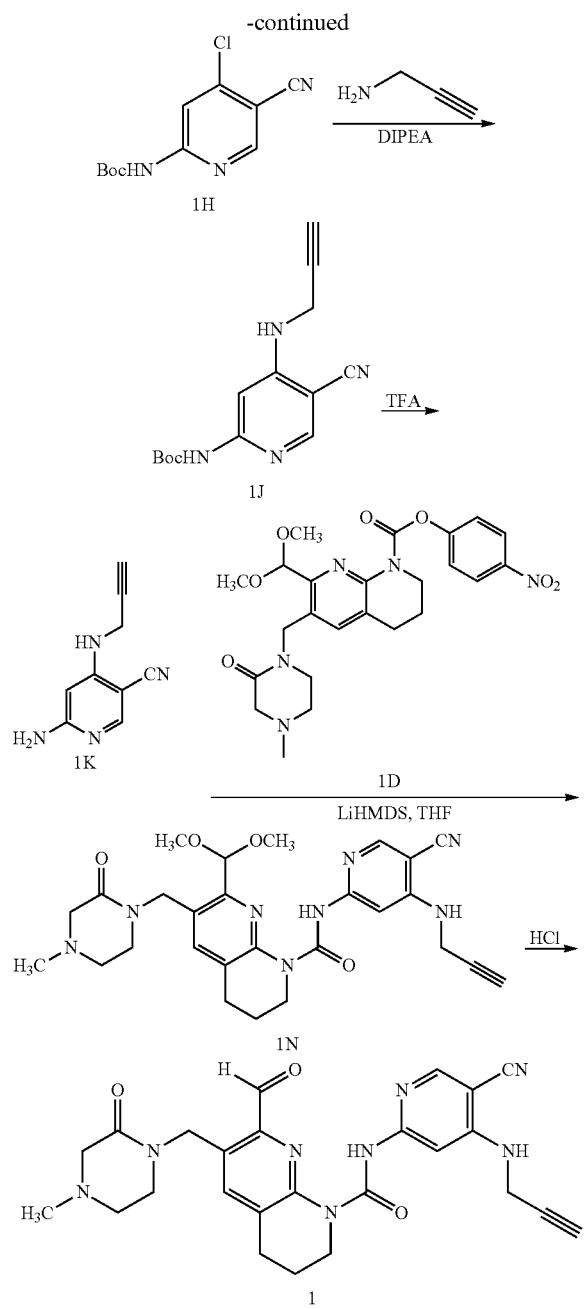

Compound N¹-methyl-N²-tert-butoxycarbonylethylenediamine (10.0 g, 57.4 mmol) was dissolved in tetrahydrofuran (100 ml), then triethylamine (8.4 ml, 60 mmol) was added. The resulting mixture was cooled to 0° C. Then, ethyl bromoacetate (6.31 ml, 57.4 mmol) was added dropwise, and the reaction was continued after the dropwise addition. TLC monitoring was conducted until the reaction was completed. The reaction mixture was concentrated, water was added and then the resulting mixture was extracted with dichloromethane twice. The organic phase was washed with saturated aqueous solution of ammonium chloride, water and saturated saline respectively, dried over anhydrous sodium sulfate, filtered and concentrated, and then subjected to column chromatography, to obtain the target product (13.4 g). The product was dissolved in dichloromethane (20 ml), trifluoroacetic acid (10 ml) was added, and the mixture was reacted at room temperature for 8 hours, then concentrated under reduced pressure to give the crude trifluoroacetate (20.5 g) of compound 1A.

Compound 1B (4.73 g, 20 mmol) (prepared according to published patent document WO 2015059668 and identified) and trifluoroacetate of compound 1A (5.43 g, 18.8 mmol) were dissolved in 1,2-dichloroethane (50 ml). Then, triethylamine (8.36 ml, 60 mmol) was added and stirred for 0.5 hour, and sodium triacetoxyborohydride (8.48 g, 40 mmol) was added in batches and stirring was continued. TLC monitoring was conducted until the reaction was completed. The reaction mixture was quenched by adding saturated aqueous solution of ammonium chloride and extracted with dichloromethane. The organic phase was pooled, dried over anhydrous sodium sulfate, filtered and concentrated, to give the compound 1C (4.5 g), ¹H NMR (400 MHz, CDCl₃) δ 7.09 (s, 1H), 5.19(s, 1H), 4.95(s, 1H), 4.70 (s, 2H), 3.41-3.37 (m, 8H), 3.22-3.18 (m, 4H), 2.70-2.67 (m, 2H), 2.59-2.56 (m, 2H), 2.23 (s, 3H), 1.91-1.85 (m, 2H); ESI-MS m/z: 335.2 [M+H]⁺.

Compound 1C (1.0 g, 3.0 mmol) was dissolved in dichloromethane (10 ml), then DIPEA (744 μl, 4.5 mmol) was added, cooled to 0° C., and a solution of p-nitrophenyl chloroformate (907 mg, 4.5 mmol) in dichloromethane (5 ml) was added dropwise, recovered to room temperature to react. After the reaction was completed, saturated aqueous solution of ammonium chloride was added and the resulting mixture was extracted with dichloromethane. The organic phase was pooled, washed with saturated saline, dried over anhydrous sodium sulfate, filtered, concentrated and subjected to column chromatography, to give the compound 1D (989 mg). Prepare a large number of 1D for use according to the above method. NMR data of the compound 1D is: ¹H NMR (400 MHz, CDCl₃) δ 8.28-8.26 (d, J=8 Hz, 2H), 7.39-7.37 (d, J=8 Hz, 2H), 5.19 (s, 1H), 4.88 (s, 2H), 3.95-3.92 (m, 2H), 3.38 (s, 6H), 3.30-3.27 (m, 2H), 3.22 (s, 2H), 2.85-2.81 (m, 2H), 2.64-2.61 (m, 2H), 2.36 (s, 3H), 2.08-2.01 (m, 2H).

In a 1 L round bottom flask, 50 g (388.9 mmol) of the starting material compound 1E was dissolved in 500 ml of DMF, cooled to 0° C. in an ice bath, and 87.5 g (388.9 mmol) of the starting material N-iodosuccinimide was slowly added in batches. The reaction mixture was transparent and clear, and after 10 min, the reaction temperature was recovered to room temperature, and the reaction was conducted under stirring overnight. TLC monitored the progress of the reaction until the reaction was completed, then the reaction mixture was slowly poured into 5 L of ice water under stirring, and a large amount of earth yellow solid was precipitated, filtered, washed with water and dried to give an earth yellow solid product 1F, which was to be taken to the next reaction, ESI-MS m/z: 255.4 [M+H]⁺.

In a one-neck round bottom flask, 90.7 g (357.1 mmol) of compound 1F was added to 500 ml of NMP, and 21.4 g (182.1 mmol) of Zn(CN)₂ was added, and 41 g (35.7 mmol) of Pd(PPh₃)₄ was quickly added, reacted at 135° C. for 5 h. After the reaction was completed, a brown oily liquid was given. The reaction mixture was slowly poured into 3 L of ice water under stirring, and a large amount of tan solid was precipitated, filtered, washed with water and dried to give compound 1G, ESI-MS m/z: 154.2 [M+H]⁺.

In a 1 L round bottom three-necked flask, 24 g (156.3 mmol) of starting material 1G was dissolved in 400 ml of anhydrous THF, and 117 ml (234.4 mmol) of LiHMDS (concentration: 2 mol/L) was added at 0° C. under the protection of N₂. The reaction was conducted under stirring at 0° C. for 2 h, and 40.9 g (187.5 mmol) of Boc₂O was added and warmed to room temperature. The reaction was carried out overnight. After the reaction was completed, the reaction was quenched with 20 ml of water. THF was removed by rotary evaporation, water was added. The mixture was extracted with ethyl acetate, washed with water, dried over MgSO$_4$, filtered, dried by rotary evaporation, and subjected to silica gel column chromatography to give product 1H, ESI-MS m/z: 254.2 [M+H]$^+$.

In a one-neck round bottom flask, 10 g (39.5 mmol) of starting material compound 1H was added, and dissolved in 30 ml of DMSO, and a total of 11.2 g (86.9 mmol) of DIPEA and 10.9 g (197.5 mmol) of propargylamine were successively added, and the reaction was carried out at 70° C. overnight. After the reaction was completed, the reaction mixture was cooled, a large amount of white solid was precipitated, filtered, washed with water and dried to give product 1J, $^1$H NMR (400 MHz, CDCl$_3$) δ 8.24 (s, 1H), 7.39 (s, 1H), 4.12-4.10 (m, 2H), 2.36-2.35 (m, 1H), 1.55 (s, 9H).

Into the reaction vessel, 5 g (18.4 mmol) of compound 1J was added, dissolved in 30 ml of dichloromethane, 30 ml of trifluoroacetic acid was added, and the reaction was carried out at 40° C. After 0.5 h, the reaction mixture was dried by rotary evaporation and adjusted to pH=8 with saturated NaHCO$_3$ solution. The mixture was extracted with ethyl acetate, washed with water, dried over MgSO$_4$, filtered, dried by rotary evaporation to give white product 1K, $^1$H NMR (400 MHz, CD$_3$OD) δ 7.93 (s, 1H), 5.85 (s, 1H), 3.99 (s, 2H), 3.31-3.30 (m, 1H).

1D (5.8 g, 11.6 mmol) and 1K (2.5 g, 14.5 mmol) were dissolved in anhydrous THF and protected by filling nitrogen gas. Then, the mixture was stirred in a cold trap at −25° C., and LiHMDS (30 ml, 1 mol/L in THF, 30 mmol) was slowly added dropwise to the reaction mixture at this temperature, and the reaction was conducted under stirring for two hours at this temperature, and then naturally recovered to room temperature and carried out overnight. The reaction was monitored by a thin layer chromatography plate until the reaction was completed, then the reaction was quenched by adding saturated NH$_4$Cl solution. The mixture was extracted with ethyl acetate, dried, concentrated and subjected to column chromatography purification to give compound 1N. $^1$H NMR (400 MHz, CDCl$_3$) δ 13.83 (s, 1H), 8.26 (s, 1H), 7.69 (s, 1H), 7.49 (s, 1H), 5.14-5.12 (m, 1H), 4.87 (s, 2H), 4.15-4.13 (m, 2H), 4.07-4.04 (m, 2H), 3.51 (s, 6H), 3.32-3.30 (m, 2H), 3.26 (s, 2H), 2.86-2.83 (m, 2H), 2.69-2.67 (m, 2H), 2.41 (s, 3H), 2.39-2.37 (m, 1H), 2.01-1.99 (m, 2H).

Compound 1N (4 g) was dissolved in THF and then a 3N HCl solution was slowly added. The reaction was conducted under stirring at room temperature for two hours and the reaction was monitored by a thin layer chromatography plate until the reaction was completed, then the pH was adjusted to be alkaline with a saturated NaHCO$_3$ solution. At this time, a large amount of white solid was precipitated, and after filtration and dryness, the solid was collected as the compound 1. $^1$H NMR (400 MHz, CDCl$_3$) δ 13.68 (s, 1H), 10.23 (s, 1H), 8.22 (s, 1H), 7.68 (s, 1H), 7.63 (s, 1H), 5.29-5.26 (m, 1H), 5.09 (s, 2H), 4.15-4.13 (m, 2H), 4.11-4.08 (m, 2H), 3.37-3.35 (m, 2H), 3.21 (s, 2H), 2.95-2.92 (m, 2H), 2.68-2.65 (m, 2H), 2.38-2.36 (m, 4H), 2.06-2.03 (m, 2H); $^{13}$C NMR (100 MHz, CDCl$_3$) δ 193.6, 167.6, 156.0, 154.9, 152.68, 152.61, 150.9, 143.9, 140.2, 128.5, 128.2, 116.3, 93.5, 90.6, 78.1, 73.1, 59.2, 51.8, 47.2, 45.1, 44.0, 43.8, 32.5, 28.4, 20.9; ESI-MS m/z: 487.4 [M+H]$^+$.

EXAMPLE 2

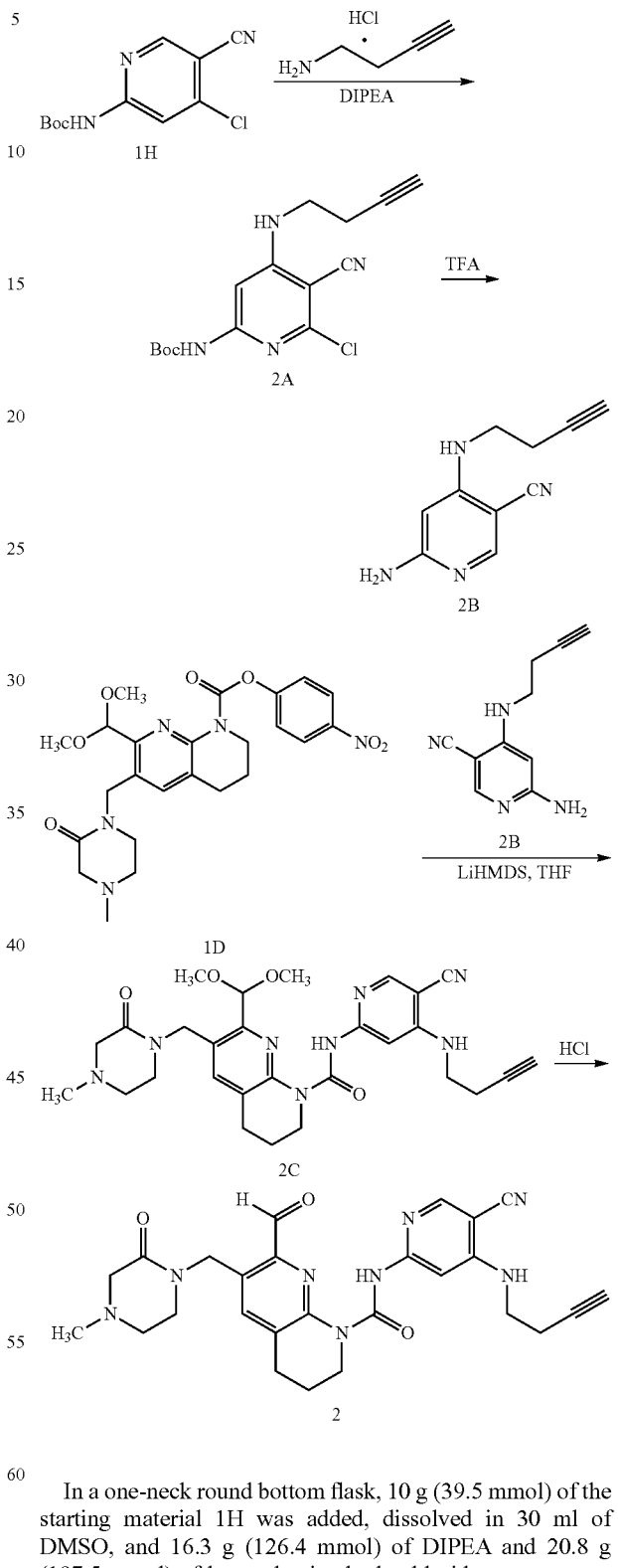

In a one-neck round bottom flask, 10 g (39.5 mmol) of the starting material 1H was added, dissolved in 30 ml of DMSO, and 16.3 g (126.4 mmol) of DIPEA and 20.8 g (197.5 mmol) of butynylamine hydrochloride were successively added. The reaction was carried out at 70° C. overnight. After TLC showed that the reaction was completed, the reaction mixture was cooled. A large amount of white solid was precipitated, filtered, and washed with water to give product 2A, which was to be taken to the next reaction. ESI-MS m/z: 287.2 [M+H]⁺.

In a one-neck round bottom flask, 5 g (17.5 mmol) of starting material 2A was added, dissolved in 30 ml of dichloromethane, 30 ml of trifluoroacetic acid was added, and the reaction was carried out at 40° C. After 0.5 h, the reaction mixture was dried by rotary evaporation and adjusted to pH=8 with a saturated NaHCO₃ solution. The mixture was extracted with ethyl acetate, washed with water, dried over MgSO₄, filtered and concentrated to give white pure product 2B, ESI-MS m/z: 187.1 [M+H]⁺.

1D (5.8 g, 11.6 mmol) and 2B (2.5 g, 13.4 mmol) were dissolved in anhydrous THF and protected by filling nitrogen gas. Then, the mixture was stirred in a cold trap at −25° C., and LiHMDS (30 ml, 1 mol/L in THF, 30 mmol) was slowly added dropwise to the reaction mixture at this temperature, and the reaction was conducted under stirring for two hours at this temperature, and then naturally recovered to room temperature and carried out overnight. The reaction was monitored by a thin layer chromatography plate until the reaction was completed, then the reaction was quenched by adding saturated NH₄Cl solution. The mixture was extracted with ethyl acetate, dried, concentrated and subjected to column chromatography purification to give compound 2C, ESI-MS m/z: 547.3 [M+H]⁺.

Compound 2C (3.5 g) was dissolved in THF and then a 3N HCl solution was slowly added. The reaction was conducted under stirring at room temperature for two hours and the reaction was monitored by a thin layer chromatography plate until the reaction was completed, then the pH was adjusted to be alkaline with a saturated NaHCO₃ solution. At this time, a large amount of white solid was precipitated, filtered, and the solid was dried under vacuum overnight, and the solid was collected as compound 2. ¹H NMR (400 MHz, CDCl₃) δ 13.64 (s, 1H), 10.24 (s, 1H), 8.20 (s, 1H), 7.63 (s, 1H), 7.28 (s, 1H), 5.28-5.26 (m, 1H), 5.10 (s, 2H), 4.10-4.07 (m, 2H), 3.55-3.52 (m, 2H), 3.38-3.35 (m, 2H), 3.21 (s, 2H), 2.95-2.92 (m, 2H), 2.68-2.66 (m, 2H), 2.62-2.58 (m, 2H), 2.36 (s, 3H), 2.13-2.12 (m, 1H), 2.07-2.01 (m, 2H); ¹³C NMR (100 MHz, CDCl₃) δ 193.6, 167.6, 155.9, 155.4, 152.74, 152.73, 150.9, 143.9, 140.2, 128.5, 128.2, 116.5, 93.1, 89.9, 80.2, 71.2, 59.3, 51.8, 47.2, 45.1, 43.9, 43.7, 41.1, 28.5, 20.9, 18.8; ESI-MS m/z: 501.3 [M+H]⁺.

EXAMPLE 3

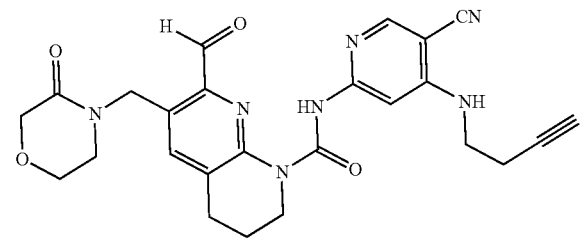

3

For the preparation of the compound 3 of the present invention, an intermediate 3A was prepared according to the published patent document WO2015059668 and the intermediate 3A was identified,

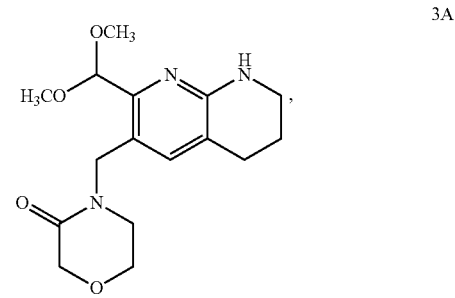 [SMILES: COC(OC)c1nc2c(cc1CN1CCOCC1=O)CCCN2]

3A the compound 3 was then prepared from 3A and the intermediate 2B according to a similar scheme to Example 2, ESI-MS m/z: 488.3 [M+H]⁺.

EXAMPLE 4

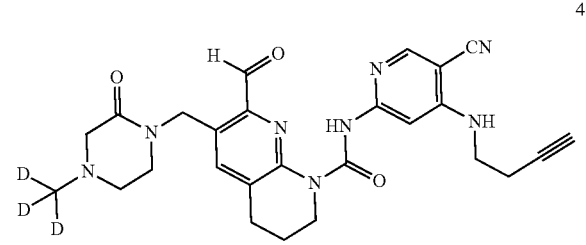 [SMILES: [2H]C([2H])([2H])N1CCN(Cc2cc3c(nc2C=O)N(C(=O)Nc2cc(NCCC#C)c(C#N)cn2)CCC3)C(=O)C1]

4

For the preparation of the compound 4 of the present invention, the intermediate 4CD was first prepared according to the similar scheme to Example 1, and the structure was as follows:

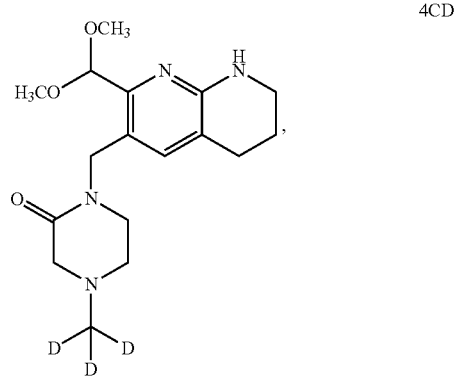 [SMILES: [2H]C([2H])([2H])N1CCN(Cc2cc3c(nc2C(OC)OC)NCCC3)C(=O)C1]

4CD

¹H NMR (400 MHz, CDCl₃) δ 7.09 (s, 1H), 5.18(s, 1H), 5.03(s, 1H), 4.70 (s, 2H), 3.40-3.37 (m, 8H), 3.22-3.17 (m, 4H), 2.70-2.67 (m, 2H), 2.58-2.55 (m, 2H), 1.91-1.85 (m, 2H); ESI-MS m/z: 338.1 [M+H]⁺. The compound 4 was then prepared from 4CD and the intermediate 2B according to a similar scheme to Example 2, ESI-MS m/z: 504.1 [M+H]⁺.

EXAMPLE 5

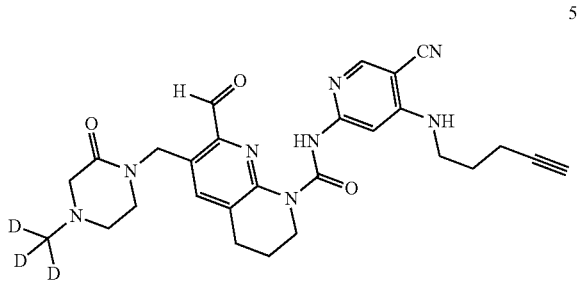 [SMILES: [2H]C([2H])([2H])N1CCN(Cc2cc3c(nc2C=O)N(C(=O)Nc2cc(NCCCC#C)c(C#N)cn2)CCC3)C(=O)C1]

For the preparation of the compound 5 of the present invention, the intermediate 4CD was first prepared according to the similar scheme to Example 1, and the compound 5 was then prepared from 4CD and the compound 4-pentyn-1-amine according to a scheme similar to Example 1, ESI-MS m/z: 518.1 [M+H]$^+$.

EXAMPLE 6

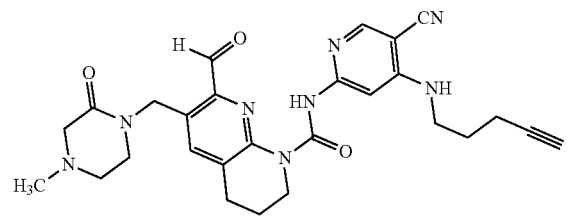

For the preparation of the compound 6 of the present invention, the intermediate 1C was first prepared according to the preparation scheme of Example 1, and the compound 6 was then prepared from 1C and the compound 4-pentyn-1-amine according to a preparation scheme similar to Example 1, ESI-MS m/z: 515.1 [M+H]$^+$.

EXAMPLE 7

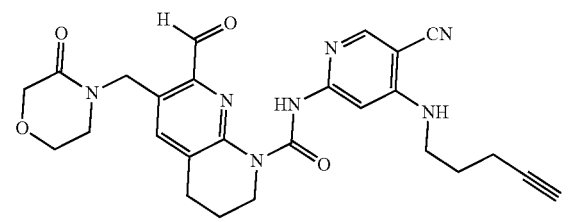

For the preparation of the compound 7 of the present invention, the key intermediate 3A was prepared according to the published patent document WO2015059668 and identified, and the compound 7 was then prepared from the compound 3A and the compound 4-pentyn-1-amine according to a similar scheme to Example 1, ESI-MS m/z: 502.2 [M+H]$^+$.

EXAMPLE 8

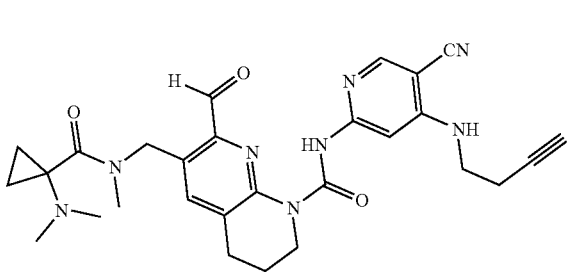

For the preparation of the compound 8 of the present invention, the intermediate 8C was first prepared according to the following scheme,

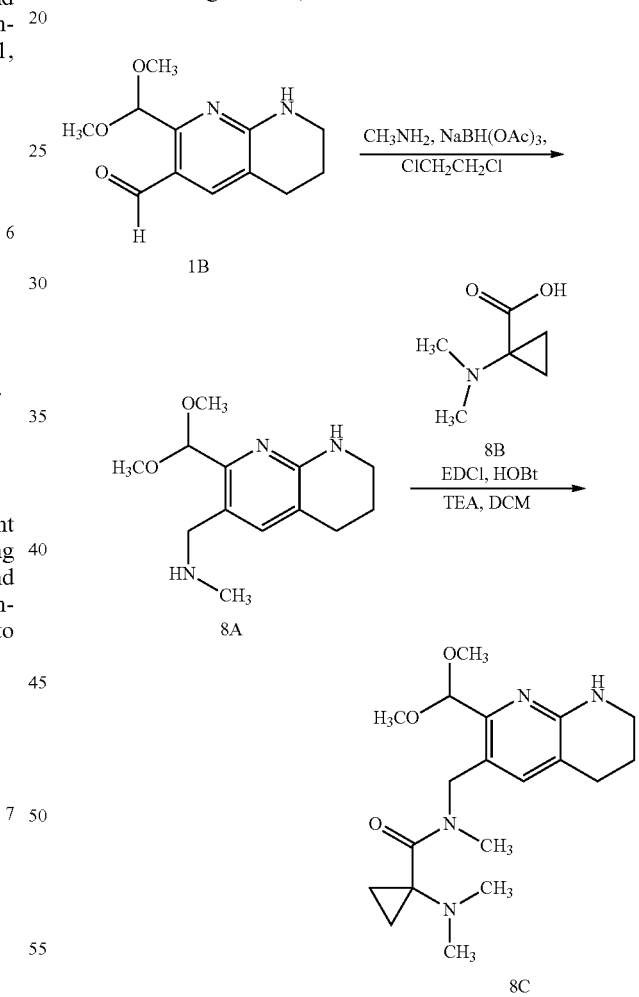

Compound 1B (prepared according to the published patent document WO2015059668 and identified) (5.9 g, 25.0 mmol) was dissolved in 1,2-dichloroethane (100 ml), then methylamine (2.0 M in THF, 50 ml, 100.0 mmol) was added. Sodium triacetoxyborohydride (10.6 g, 50.0 mmol) was added in batches at 0° C. The reaction was recovered to room temperature. The reaction was monitored by thin layer chromatography until the reaction was completed, then the reaction was quenched by adding saturated aqueous solution of NH$_4$Cl. The mixture was concentrated and the organic solvent was removed. Impurities were removed by ethyl acetate extraction and the target product in ethyl acetate was extracted with water. The aqueous phase was combined and saturated aqueous solution of sodium bicarbonate was added to adjust the water phase to weak alkali. The mixture was extracted three times with dichloromethane, and the organic phase was combined, washed with saturated saline, dried over anhydrous sodium sulfate, filtered and concentrated to give compound 8A, ESI-MS m/z: 252.2 [M+H]$^+$.

Compound 8A (4.46 g, 17.8 mmol) and compound 8B (2.30 g, 17.8 mmol) were dissolved in dichloromethane (50 ml). EDCI (3.41 g, 17.8 mmol), HOBt (2.41 g, 17.8 mmol) and triethylamine (3.72 ml, 26.7 mmol) were added respectively at 0° C. The reaction was warmed to room temperature. The reaction was monitored by thin layer chromatography until the reaction was completed, then the reaction mixture was concentrated under reduced pressure. Saturated aqueous solution of sodium bicarbonate was added. The mixture was extracted with ethyl acetate, dried over anhydrous sodium sulfate, filtered and concentrated to give compound 8C, ESI-MS m/z: 363.1 [M+H]$^+$.

The compound 8 was then prepared from 8C and the intermediate 2B according to a similar scheme to Example 2, ESI-MS m/z: 529.1 [M+H]$^+$.

EXAMPLE 9

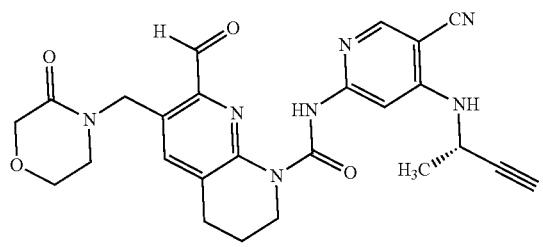

9

For the preparation of the compound 9 of the present invention, the key intermediate 3A was prepared according to the published patent document WO2015059668 and identified, and the compound 9 was then prepared from the compound 3A and the compound (S)-3-butyn-2-amine according to a similar scheme to Example 1, ESI-MS m/z: 488.2 [M+H]$^+$.

EXAMPLE 10

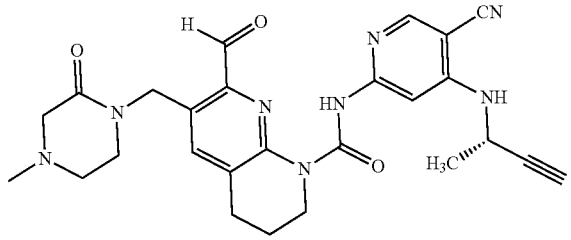

10

For the preparation of the compound 10 of the present invention, the key intermediate 1C was prepared according to the preparation scheme of Example 1, and the compound 10 was then prepared from 1C and the compound (S)-3-butyn-2-amine according to a similar preparation scheme to Example 1, ESI-MS m/z: 501.2 [M+H]$^+$.

Biological Tests

BIOLOGICAL TEST EXAMPLE 1

Inhibition Test of Fibroblast Growth Factor Receptor (FGFR) Kinase Activity

The inhibitory activities of the test substances on FGFR kinase were determined by the ADP-Glo method. The human FGFR1, FGFR2 and FGFR4 kinase recombinant proteins and kinase activity assay kit ADP-Glo™ were purchased from Promega, and the FGFR3 kinase recombinant protein was purchased from BPS Bioscience. The test substance, which was diluted gradiently from 1000 nM, was incubated with the FGFR1, FGFR2, FGFR3 or FGFR4 kinase recombinant protein for 30 minutes, reacted with the substrate in the presence of ATP, and ADP-Glo™ detected the generated ADP and further produced chemiluminescence signals. Microplate reader (Perkin Elmer, Envision) were used to determine the reading for each well, and the origin 7.5 was used to calculate and analyze the IC50, i.e. the concentration at which 50% inhibition occurred.

The inhibition of the compounds of the present invention on FGFR1-4 kinase activity was measured by the above test, and the measured IC50 (nM) values are shown in Table 1.

TABLE 1

| Compound No. | FGFR4 | FGFR1 | FGFR2 | FGFR3 |
| --- | --- | --- | --- | --- |
| Compound 1 | 0.41 | >1000 | >1000 | >1000 |
| Compound 2 | 0.33 | >1000 | >1000 | >1000 |
| Compound 3 | 0.62 | >1000 | >1000 | >1000 |
| Compound 4 | 0.37 | >1000 | >1000 | >1000 |
| Compound 6 | 0.59 | >1000 | >1000 | >1000 |

BIOLOGICAL TEST EXAMPLE 2

Inhibition Activity Test of the Proliferation of Hepatocellular Carcinoma (HCC) Cell Lines The inhibitory activities of the compounds of the examples on cell proliferation in vitro were tested using five hepatocellular carcinoma cell lines: Hep3B, Huh7, JHH-7, SK-hep-1, SNU423. The above cells were all from ATCC (American Type Culture Collection). Among them, Hep3B, Huh-7, JHH-7 these three cell lines all have FGF19 gene amplification (increased copy number) and increased mRNA expression level, as well as high level expression of FGFR4 and KLB gene mRNA; SK-hep-1, SNU423 cell lines have no FGF19 gene amplification and the expression level of FGF19 mRNA was very low (Barretina J, Caponigro G, et al. Nature 2012; 483: 603-7.).

Cell proliferation was measured using the SRB (Sulforhodamine-B, sulforhodamine B) method. The cells were cultured to a cell fusion of more than 90% and then trypsinized. After counting, the cells were inoculated into 96-well plates at 6000 cells/well. After adherent culture overnight, the test compound was dissolved in DMSO and diluted with complete medium, added to the culture wells to form a 5-fold dilution of 10 concentration gradients from 10 μM. The cells were incubated for further 72 hours, 50 μl of 50% trichloroacetic acid was added to each well and fixed at 4° C. for 1 hour. The trichloroacetic acid in each well was discarded and washed 5 times with 300 µl of double distilled water. After drying at room temperature, 50 µl of 0.4% SRB dye solution (1% acetic acid/0.4% SRB) was added to each well to react for 15 min. The dye solution of each well was discarded, washed 6-7 times with 1% acetic acid, and dried at room temperature. 200 µl of 10 mM Tris solution (pH=10.5) was added to each well and shaken until the solution was clear. The absorbance at 490 nm of each well was measured by a microplate reader. The reading of the wells where the concentration of the test compound was 0 was used as a control, and fitted with Origin 7.5 software, the IC50 value (nM) of the test substance for inhibiting cell proliferation was calculated.

The antitumor cell proliferation activities of the compounds of the present invention were measured by the above test, and the measured IC50 (nM) values are shown in Table 2.

TABLE 2

| Compound No. | Hep3B | HUH-7 | JHH-7 | SNU387 | SK-hep-1 |
| --- | --- | --- | --- | --- | --- |
| Compound 1 | 0.35 | 4.0 | 3.0 | >1000 | >1000 |
| Compound 2 | 0.40 | 2.9 | 2.6 | >1000 | >1000 |
| Compound 3 | 0.62 | 5.7 | N.D. | >1000 | N.D. |
| Compound 4 | 0.36 | 2.8 | N.D. | >1000 | N.D. |
| Compound 6 | 0.53 | 4.9 | N.D. | >1000 | N.D. |

N.D. means not determined.

The above data indicates that the compounds 1, 2, 3, 4, 6 of the present invention have a significant selective inhibitory effect on HCC cells with FGF19 gene amplification.

BIOLOGICAL TEST EXAMPLE 3

HCC Cell Subcutaneous Transplantation Tumor Growth Inhibition Test in Nude Mice

The Hep3B cells in the logarithmic growth phase were cultured and collected, and subcutaneously inoculated into the right back of nude mice (female Balb/c Nude mice, from Beijing Vitalriver) at $1\times10^7$ cells/mouse. When the tumor grew to 50-300 mm$^3$, tumor-bearing nude mice were randomly grouped, 6 animals per group. Subsequently, each group of animals was administered at the following dose, and the day of the first dose was defined as the first day of the test.

Blank solvent (ultra-pure water) control group, compound 1, compound 2 were respectively set to 50 mg/kg, 100 mg/kg, 150 mg/kg three dose groups, intragastric administration, twice a day (BID), for 21 consecutive days. The state of the animals was observed daily during the administration; the body weight was measured once a week before the first administration; and the body weight was measured twice a week after the start of the administration. The size of the transplantation tumor was measured every 3 days after the start of administration. Tumor volume $(TV)=\frac{1}{2}\times a\times b^2$, wherein, a and b represent the length and width of the tumor, respectively. The relative tumor volume (RTV) was calculated based on the measured results, $RTV=V_t/V_0\times100$, wherein $V_0$ is the measured tumor volume on the day of the cage (i.e., day 0), and $V_t$ is the tumor volume at each measurement.

Figure 2:
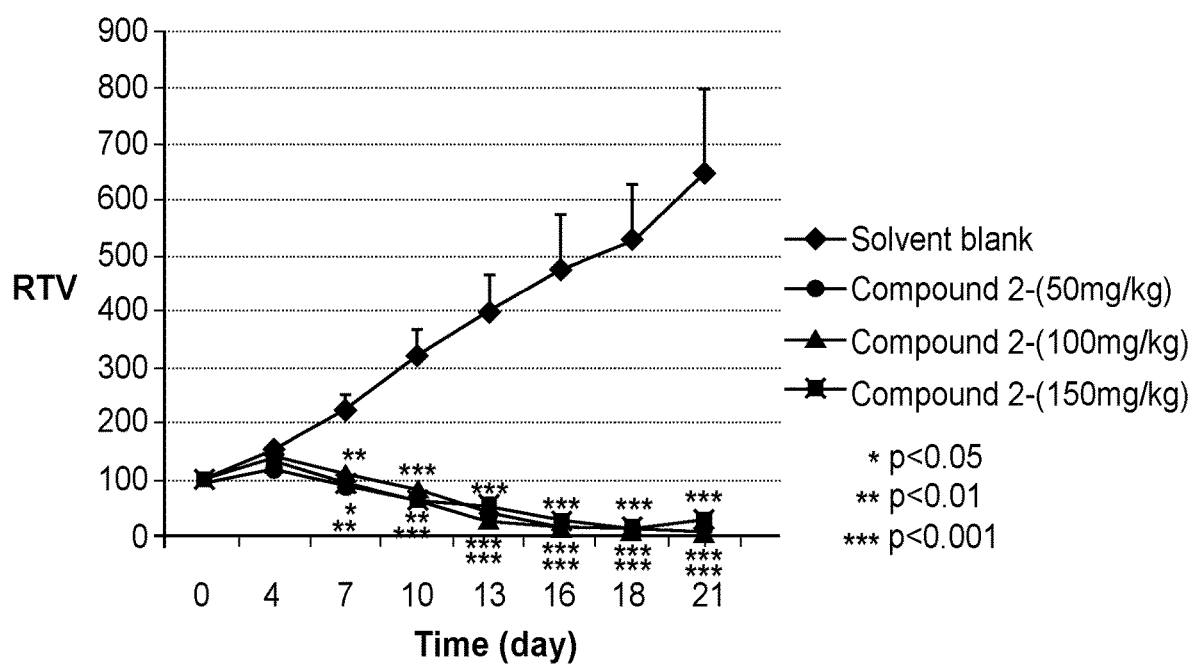
FIG. 2 shows the results of in vivo efficacy test using HEP3B cells in a hepatocellular carcinoma model. Compound 2 and solvent blank control were orally administered by intragastric gavage, and relative tumor volume during the experimental period was measured.

The growth inhibition of the test compounds on Hep3b transplantation tumor in nude mice is shown in FIG. 1, FIG. 2.

Compound 1 and compound 2 were administered at a dose of 50 mg/kg, and the growth inhibition of the transplantation tumor was significant after BID 21 days; in the animals of all the dose groups of compound 1 and compound 2, during the administration test period, the water and food take was normal, the activity was normal, the body weight was normal, and no adverse reactions occurred.

Figure 3:
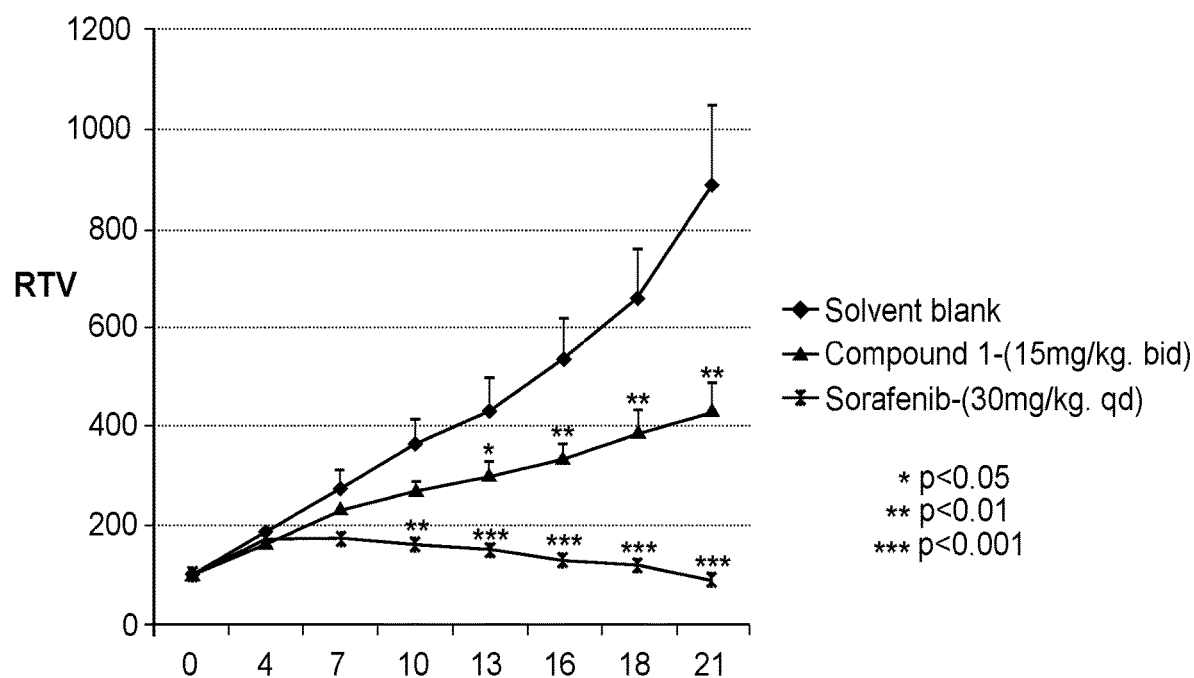
FIG. 3 shows the results of in vivo efficacy test using HEP3B cells in a hepatocellular carcinoma model. Compound 1 (15 mg/kg, bid), sorafenib (30 mg/kg, qd) and solvent blank control were orally administered by intragastric gavage, and relative tumor volume during the experimental period was measured.

After establishing the Hep3B nude mice transplantation tumor model according to the method described above, the mice were divided into three groups and intragastrically administered with a blank solvent (ultra-pure water) control, compound 1 (15 mg/kg, BID), sorafenib (prepared according to the method described in the literature CN1721397A and identified) respectively, 30 mg/kg, once a day (QD), for 21 consecutive days. The growth inhibition on the transplantation tumor of the test substances, animal status and body weight were evaluated in the same manner as above. The growth curve of the transplantation tumor of each group is shown in FIG. 3. The tumor volume (TV) was measured and the tumor inhibition rate was calculated according to the tumor inhibition rate $(TGI)=(1-T/C)\times100\%$. C: average tumor volume of the control group; T: average tumor volume of the administration group. The results are shown in Table 3. "+" indicates that the tumor inhibition rate is 40%-60%; "++" indicates that the tumor inhibition rate is 60%-80%; "+++" indicates that the tumor inhibition rate is 80%-100%.

The efficacy of compound 1 at a dose of 15 mg/kg BID was superior to that of sorafenib at a dose of 30 mg/kg QD in the Hep3B nude mouse transplantation tumor model.

TABLE 3

|  | Tumor inhibition rate (%) (the last administration) |
| --- | --- |
| Compound 1 (15 mg/kg, bid) | +++ |
| Sorafenib (30 mg/kg, qd) | + |

BIOLOGICAL TEST EXAMPLE 4

Exploration Experiment of the Tolerance Dose of Test Compounds in Mice

Female Balb/c Nude mice (from Beijing Vitalriver), weighing 18-22 g, randomized into groups, 6 mice per group, were intragastrically administered the test substances with the following doses: compound 1 (50 mg/kg, 100 mg/kg, 200 mg/kg, 500 mg/kg); compound 2 (50 mg/kg, 100 mg/kg, 200 mg/kg, 500 mg/kg). The drug was administered twice a day for 5 consecutive days. Animal status was observed daily and body weight and food intake were monitored.

During the administration period, in the animals of all the dose groups of the test compounds, the water and food take was normal, the activity was normal, the body weight was normal, and no significant adverse reactions occurred.

Biological test examples 3 and 4 suggest that compound 1 and compound 2 have better tumor suppressing effects and higher tolerence doses, and have larger safety windows.

The invention claimed is:

1. A compound of formula (I), a stereoisomer, a tautomer or a pharmaceutically acceptable salt thereof,

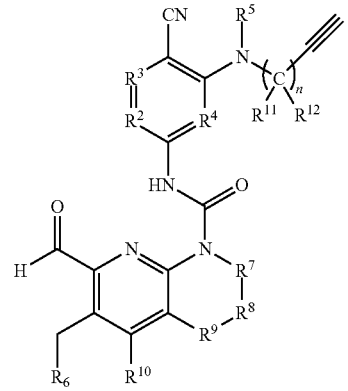
(I)

wherein, $R^2$ is N, $R^3$ and $R^4$ are CH;

$R^5$ is selected from the group consisting of hydrogen, alkyl, alkoxyl, aryl, cycloalkyl, heteroaryl, heterocyclyl and heterocyclylalkyl;

$R^6$ is selected from the group consisting of cycloalkyl heteroaryl, heterocyclyl and heterocyclylalkyl;

$R^7$, $R^8$ and $R^9$ are $CH^2$;

$R^{10}$, $R^{11}$ and $R^{12}$ are independently hydrogen, halogen, cyano, amino, hydroxyl, alkyl, alkoxyl, aryl, cycloalkyl, heteroaryl, or the two substituents $R^{11}$ and $R^{12}$ are cyclized into a cyclic group, n=1, 2, 3, 4, 5.

2. The compound of formula (I), the stereoisomer, the tautomer or the pharmaceutically acceptable salt thereof according to claim 1, comprising a compound of general formula (II),

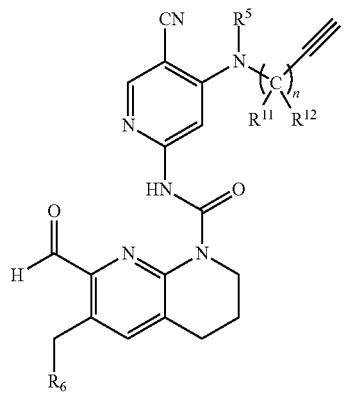
(II)

wherein $R^5$ is hydrogen, alkyl, alkoxyl, aryl, cycloalkyl, heteroaryl, heterocyclyl, heterocyclylalkyl, $R^{11}$ and $R^{12}$ are independently hydrogen, halogen, cyano, amino, hydroxyl, alkyl, alkoxyl, aryl, cycloalkyl, heteroaryl, or the two substituents $R^{11}$ and $R^{12}$ are cyclized into a cyclic group, n=1, 2, 3, 4, 5, $R^6$ is selected from the following structures:

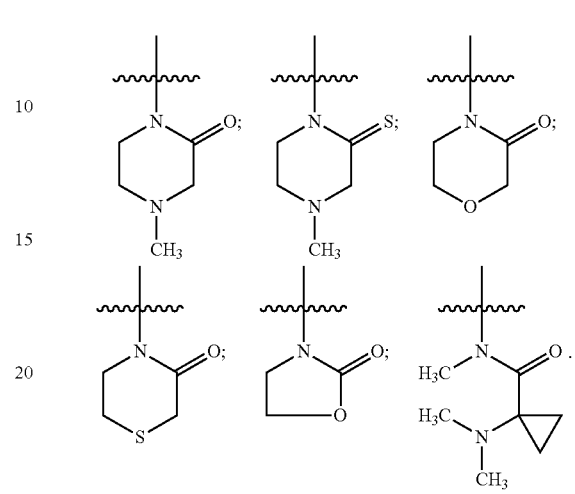

3. The compound of formula (I) according to claim 2, wherein the structure segment

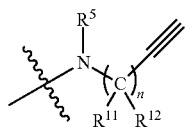

is selected from the following structures:

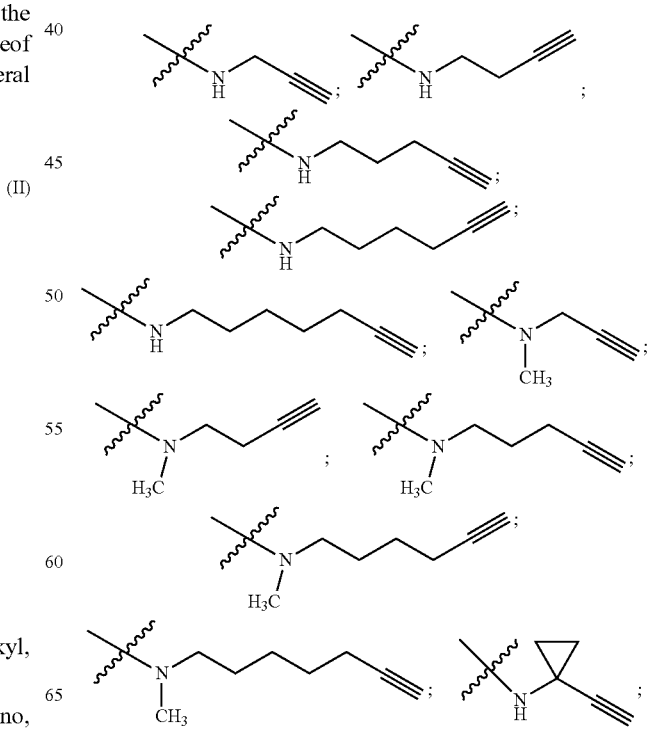

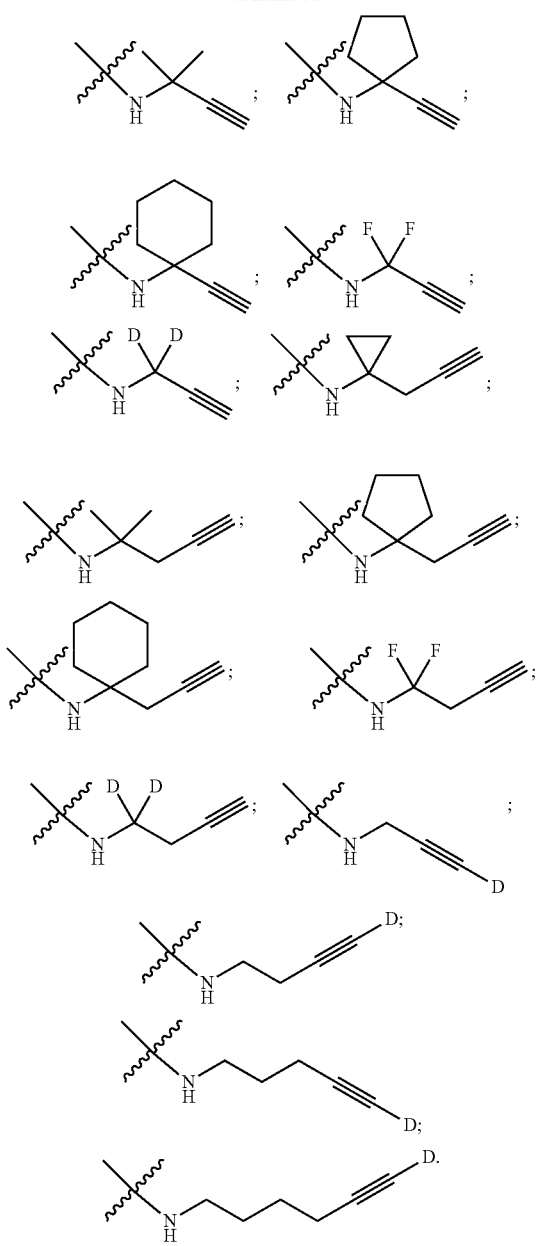
4. The compound of formula (I), the stereoisomer, the tautomer or the pharmaceutically acceptable salt thereof according to claim 1, which is selected from the group consisting of the following compounds:
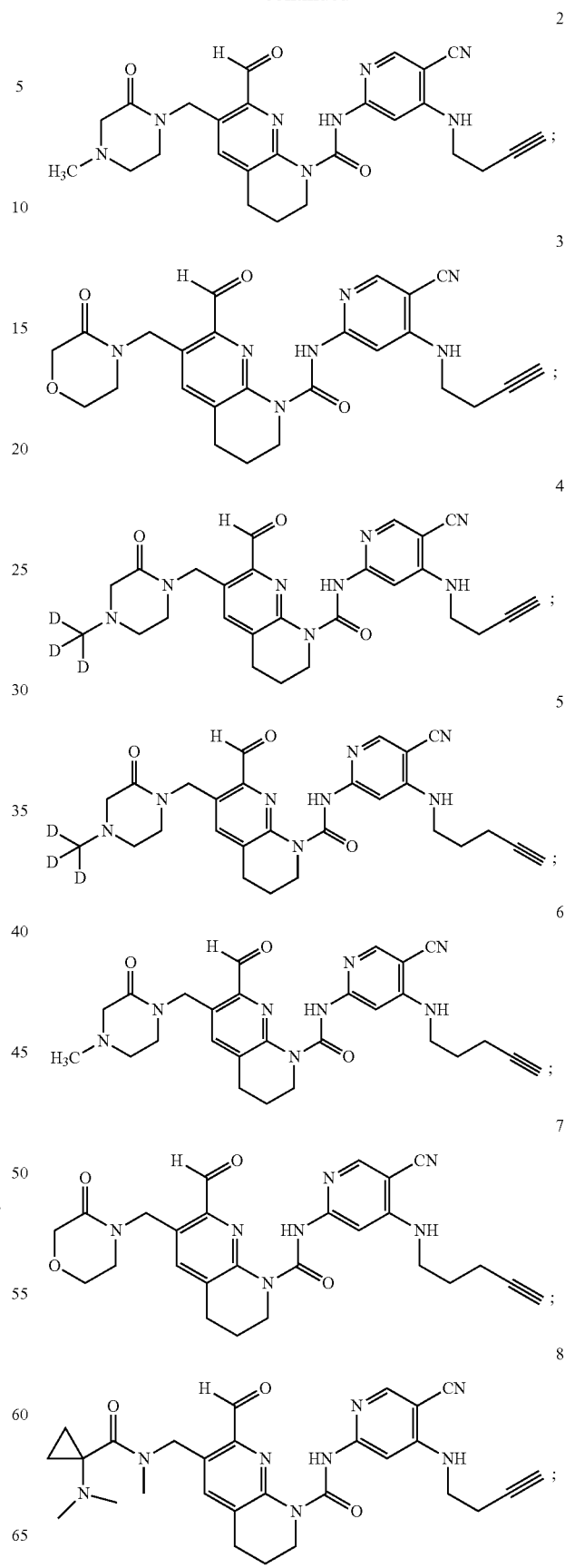

5. The compound of formula (I) the stereoisomer, the tautomer or the pharmaceutically acceptable salt thereof according to claim 1, which is selected from the group consisting of the following compounds:

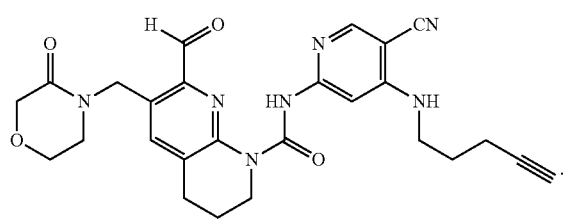

6. The compound of formula (I), the stereoisomer, the tautomer or the pharmaceutically acceptable salt thereof according to claim 1, which is selected from the group consisting of the following compounds:

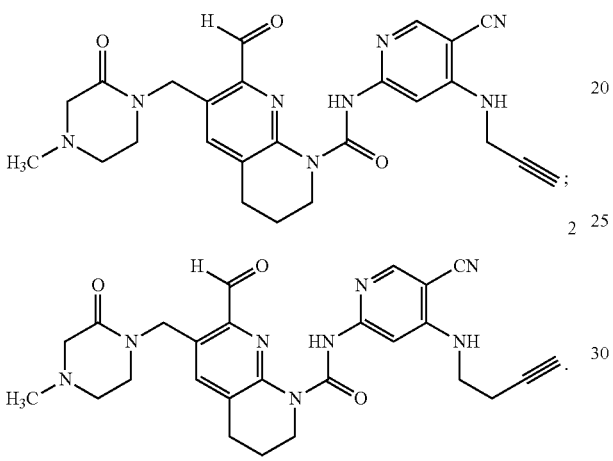

7. A method for preparing the compound, the stereoisomer, the tautomer or the pharmaceutically acceptable salt thereof according to claim 2, comprising the following steps:

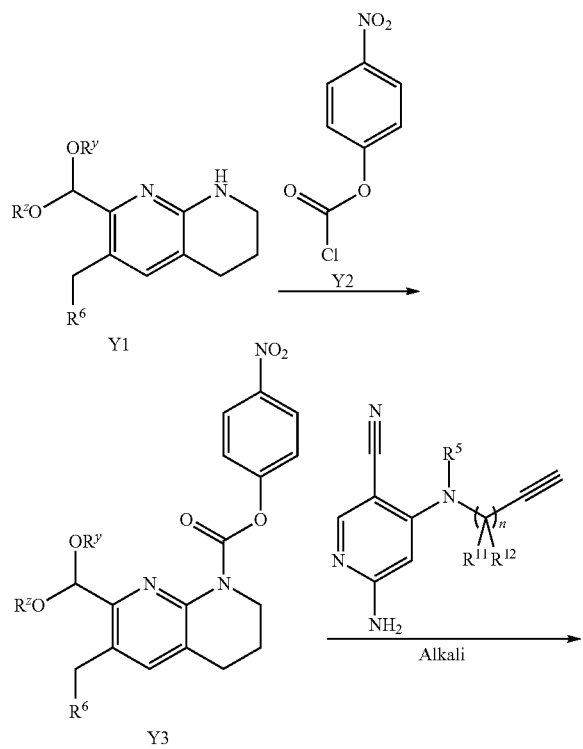

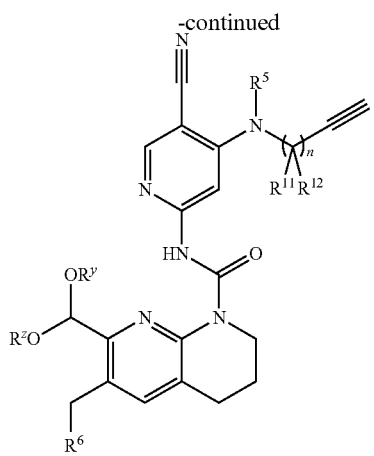

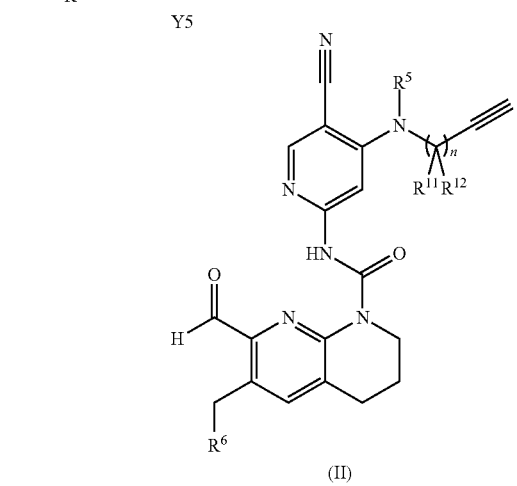

wherein, $R^5$, $R^6$, $R^{11}$, $R^{12}$ and n are as defined in claim 2; $R^y$ and $R^z$ are selected from C1-C6 alkyl groups, or $R^y$ and $R^z$ are linked to form a five- to seven-membered heterocyclic structure, comprising the following steps:

Step 1, in a solvent, at a temperature of −30 to 80° C., the compounds Y1 and Y2 are coupled under the action of an alkali to form the compound Y3, wherein the solvent is one or more selected from the group consisting of tetrahydrofuran, dioxane, dichloromethane, chloroform, tetrachloromethane, acetonitrile, dichloroethane and ethyl acetate;

Step 2, in a solvent, at a temperature of −50 to 80° C., the compounds Y3 and Y4 are reacted under the action of an alkali to obtain the compound Y5, wherein the solvent is one or more selected from the group consisting of tert-butyl methyl ether, diethyl ether, tetrahydrofuran, dioxane, dichloromethane, chloroform, acetonitrile and dichloroethane;

Step 3, in a solvent, at a temperature of −30 to 80° C., the compound Y5 is deprotected by a deprotecting reagent to obtain the compound (II), wherein the solvent is one or more selected from the group consisting of tert-butyl methyl ether, diethyl ether, tetrahydrofuran, dioxane, dichloromethane, chloroform, tetrachloromethane, acetone, butanone, ethyl acetate and water.

8. The method according to claim 7, wherein, in step 1, the solvent is dichloromethane or chloroform; the temperature is −10 to 20° C.; the alkali is selected from the group consisting of triethylamine, N,N'-dimethylpropylamine, N,N'-diisopropylethylamine and aqueous solution of methylamine;

in step 2, the solvent is tetrahydrofuran or dioxane; the temperature is −30 to 10° C., and the alkali is selected from the group consisting of lithium bis(trimethylsilyl) amide, sodium bis(trimethylsilyl)amide and potassium bis(trimethylsilyl) amide;

in step 3, the solvent is tetrahydrofuran, water, or a mixed solution of tetrahydrofuran and water; the temperature is −10 to 10° C.; the deprotecting reagent is selected from phosphoric acid, sulfuric acid, concentrated hydrochloric acid, nitric acid, citric acid, methanesulfonic acid or p-toluenesulfonic acid.

9. A pharmaceutical composition comprising a therapeutically effective amount of the compound, or the stereoisomer, the tautomer or the pharmaceutically acceptable salt thereof according to claim 1 and a pharmaceutically acceptable carrier.

10. The pharmaceutical composition according to claim 9 for use in the treatment of a disease mediated by FGFR4 or FGF19, and the disease is liver cancer, lung cancer, gastric cancer, sarcoma, cholangiocarcinoma, prostate cancer, ovarian cancer or breast cancer.

11. A method for treating a disease mediated by FGFR4 or FGF19, comprising administering the compound, the stereoisomer, the tautomer or the pharmaceutically acceptable salt thereof according to claim 1, as a selective inhibitor of FGFR4 kinase, and the disease is liver cancer, lung cancer, gastric cancer, sarcoma, cholangiocarcinoma, prostate cancer, ovarian cancer or breast cancer.

12. A method for treating liver cancer or gastric cancer, comprising administering the compound, the stereoisomer, the tautomer or the pharmaceutically acceptable salt thereof according to claim 1 or the pharmaceutical composition according to claim 9.

13. A method for treating a disease mediated by FGFR4 or FGF19, comprising administering the compound, the stereoisomer, the tautomer or the pharmaceutically acceptable salt thereof according to claim 1 as a selective inhibitor of FGFR4 kinase, and the disease is liver cancer or gastric cancer.

* * * * *